(12) United States Patent
Zhou et al.

(10) Patent No.: US 8,735,096 B2
(45) Date of Patent: May 27, 2014

(54) OPTICAL CONTROL OF PROTEIN ACTIVITY AND LOCALIZATION BY FUSION TO PHOTOCHROMIC PROTEIN DOMAINS

(71) Applicant: The Board of Trustees of the Leland Stanford Junior University, Palo Alto, CA (US)

(72) Inventors: Xin Zhou, Stanford, CA (US); Michael Z. Lin, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/848,346

(22) Filed: Mar. 21, 2013

(65) Prior Publication Data

US 2013/0252282 A1   Sep. 26, 2013

Related U.S. Application Data

(60) Provisional application No. 61/614,492, filed on Mar. 22, 2012.

(51) Int. Cl.
*C12P 21/06* (2006.01)
*C07K 1/00* (2006.01)

(52) U.S. Cl.
USPC .......................................... 435/69.1; 530/350

(58) Field of Classification Search
USPC .......................................... 530/350; 435/69.1
See application file for complete search history.

(56) References Cited

U.S. PATENT DOCUMENTS

| | | |
|---|---|---|
| 7,604,805 B2 | 10/2009 | Lim et al. |
| 7,897,385 B2 | 3/2011 | Miyawaki et al. |
| 8,034,614 B2 | 10/2011 | Miyawaki et al. |
| 8,114,843 B2 | 2/2012 | Isacoff et al. |
| 2009/0203035 A1 | 8/2009 | Shaner et al. |
| 2012/0237966 A1 | 9/2012 | Dolmetsch et al. |

FOREIGN PATENT DOCUMENTS

| | | |
|---|---|---|
| WO | 2005/010198 A2 | 2/2012 |
| WO | 2012/045733 A1 | 4/2012 |

OTHER PUBLICATIONS

Habuchi et al. (2005) Reversible single-molecule photoswitching in the GFP-like fluorescent protein Dronpa. Proc. Natl. Acad. Sci. U S A. 102(27):9511-9516.
Krauss et al. (2011) Enlightened enzymes: Strategies to create novel photoresponsive proteins. Chemistry 17:2552-2560.
Riggsbee et al. (2010) Recent advances in the photochemical control of protein function. Trends Biotechnol. 28:468-475.
Levskaya et al. (2009) Spatiotemporal control of cell signalling using a light-switchable protein interaction. Nature 461:997-1001.
Shimizu-Sato et al. (2002) A light-switchable gene promoter system. Nat. Biotechnol. 20:1041-1044.
Tyszkiewicz et al. (2008) Activation of protein splicing with light in yeast. Nat. Methods 5:303-305.
Kennedy et al. (2010) Rapid blue-light-mediated induction of protein interactions in living cells. Nat. Methods 7:973-975.
Fan et al. (2011) Improving a designed photocontrolled DNA-binding protein. Biochemistry 50:1226-1237.
Strickland et al. Light-activated DNA binding in a designed allosteric protein. Proc. Natl. Acad. Sci. U.S.A 105:10709-10714.
Wu et al. (2009) A genetically encoded photoactivatable rac controls the motility of living cells. Nature 461:104-108.
Yazawa et al. (2009) Induction of protein-protein interactions in live cells using light. Nat. Biotechnol. 27:941-945.
Moglich et al. (2010) Engineered photoreceptors as novel optogenetic tools. Photochem. Photobiol. Sci. 9:1286-1300.
Strickland et al. (2010) Rationally improving lov domain-based photoswitches. Nat. Methods 7:623-626.
Ando et al. (2004) Regulated fast nucleocytoplasmic shuttling observed by reversible protein highlighting. Science 306:1370-1373.
Mizuno et al. (2008) Light-dependent regulation of structural flexibility in a photochromic fluorescent protein. Proc Natl Acad. Sci. U.S.A. 105:9227-9232.
Wu et al. (2011) Spatiotemporal control of small gtpases with light using the lov domain. Methods Enzymol 497:393-407.
Andresen et al. (2008) Photoswitchable fluorescent proteins enable monochromatic multilabel imaging and dual color fluorescence nanoscopy. Nat Biotechnol. 26(9):1035-1040.
Pletnev et al. (2012) A structural basis for reversible photoswitching of absorbance spectra in red fluorescent protein rsTagRFP. J. Mol. Biol. 417(3):144-151.
Shaner et al. (2008) Improving the photostability of bright monomeric orange and red fluorescent proteins. Nat. Methods. 5(6):545-551.

*Primary Examiner* — Maryam Monshipouri
(74) *Attorney, Agent, or Firm* — Jenny Buchbinder

(57) ABSTRACT

Engineered fusion proteins comprising photochromic protein domains are disclosed. In particular, the inventors have constructed fusion proteins containing photoswitchable photochromic fluorescent protein domains linked to selected proteins and shown that such fusion proteins can be used to control the activity or localization of selected proteins with light.

17 Claims, 35 Drawing Sheets

K-CAAX
| Dronpa 145K | CAAX |

K-I-CAAX
| Dronpa 145K | 5aa | ITSN DH | 15aa | CAAX |

I-K-CAAX
| ITSN DH | 15aa | Dronpa 145K | CAAX |

N-I-N-CAAX
| Dronpa 145N | 5aa | ITSN DH | 15aa | Dronpa 145N | CAAX |

K-I-N-CAAX
| Dronpa 145K | 5aa | ITSN DH | 15aa | Dronpa 145N | CAAX | mNeptune-Fascin
| mNeptune | Fascin |

Figure 7B

SEQUENCE LISTING

```
<160> NUMBER OF SEQ ID NOS: 21

<210> SEQ ID NO 1
<211> LENGTH: 224
<212> TYPE: PRT
<213> ORGANISM: Artificial
<220> FEATURE:
<223> OTHER INFORMATION: Dronpa-145K

<400> SEQUENCE: 1

Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Val Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Asn Tyr Glu
                85                  90                  95

Asp Gly Gly Ile Cys Asn Ala Thr Asn Asp Ile Thr Leu Asp Gly Asp
            100                 105                 110

Cys Tyr Ile Tyr Glu Ile Arg Phe Asp Gly Val Asn Phe Pro Ala Asn
        115                 120                 125

Gly Pro Val Met Gln Lys Arg Thr Val Lys Trp Glu Pro Ser Thr Glu
    130                 135                 140

Lys Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His His Ile Glu Ile Lys Ser His Asp Lys Asp Tyr Ser Asn Val Asn
        195                 200                 205

Leu His Glu His Ala Glu Ala His Ser Glu Leu Pro Arg Gln Ala Lys
    210                 215                 220

<210> SEQ ID NO 2
<211> LENGTH: 672
<212> TYPE: DNA
<213> ORGANISM: Artificial
<220> FEATURE:
<223> OTHER INFORMATION: Dronpa-145K

<400> SEQUENCE: 2
atgagcgtga tcaagcccga catgaaaatc aagctgagga tggagggtgc cgtgaacggt    60
cacccgtttg cgatcgaggg cgtgggactg ggcaagccgt tcgagggaaa gcaaagcatg   120
gacctcaagg tgaaggaggg cggaccgctg cccttcgcct acgacattct gaccactgtc   180
ttctgctacg gtaatcgcgt cttcgcaaag tatcccgaaa acatcgtgga ttactttaag   240
cagagcttcc cggagggtta ctcctgggag cgatccatga actacgagga cggagggatc   300
tgcaacgcga cgaacgatat aaccttggac ggcgactgct acatttacga aattcggttc   360
```

```
gacggcgtga atttcccagc gaatggccct gtaatgcaaa aacgcacggt aaagtgggag    420
cccagcaccg agaagctgta cgtccgcgac ggagtcctga agggagacgt gaacatggcg    480
ctttcattgg aagtggcgg gcactacaga tgcgatttca agacgaccta taaggcgaaa    540
aaggtggtcc aactgccgga ctaccatttc gtcgaccacc acatcgagat caagagccac    600
gacaaagact atagcaacgt gaatctccac gagcatgccg aggcccacag cgagctgccc    660
aggcaggcca ag                                                       672
```

<210> SEQ ID NO 3
<211> LENGTH: 224
<212> TYPE: PRT
<213> ORGANISM: Artificial
<220> FEATURE:
<223> OTHER INFORMATION: Dronpa-145N

<400> SEQUENCE: 3

```
Met Ser Val Ile Lys Pro Asp Met Lys Ile Lys Leu Arg Met Glu Gly
 1               5                  10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Thr Val Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met Asn Tyr Glu
                85                  90                  95

Asp Gly Gly Ile Cys Asn Ala Thr Asn Asp Ile Thr Leu Asp Gly Asp
           100                 105                 110

Cys Tyr Ile Tyr Glu Ile Arg Phe Asp Gly Val Asn Phe Pro Ala Asn
       115                 120                 125

Gly Pro Val Met Gln Lys Arg Thr Val Lys Trp Glu Pro Ser Thr Glu
   130                 135                 140

Asn Leu Tyr Val Arg Asp Gly Val Leu Lys Gly Asp Val Asn Met Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Phe Val Asp
            180                 185                 190

His His Ile Glu Ile Lys Ser His Asp Lys Asp Tyr Ser Asn Val Asn
        195                 200                 205

Leu His Glu His Ala Glu Ala His Ser Glu Leu Pro Arg Gln Ala Lys
    210                 215                 220
```

<210> SEQ ID NO 4
<211> LENGTH: 672
<212> TYPE: DNA
<213> ORGANISM: Artificial
<220> FEATURE:
<223> OTHER INFORMATION: Dronpa-145N

<400> SEQUENCE: 4

```
atgagcgtga tcaagcccga catgaaaatc aagctgagga tggagggtgc cgtgaacggt    60
cacccgtttg cgatcgaggg cgtgggactg ggcaagccgt tcgagggaaa gcaaagcatg   120
gacctcaagg tgaaggaggg cggaccgctg cccttcgcct acgacattct gaccactgtc   180
```

```
ttctgctacg gtaatcgcgt cttcgcaaag tatcccgaaa acatcgtgga ttactttaag      240
cagagcttcc cggagggtta ctcctgggag cgatccatga actacgagga cggagggatc      300
tgcaacgcga cgaacgatat aaccttggac ggcgactgct acatttacga aattcggttc      360
gacggcgtga atttcccagc gaatggccct gtaatgcaaa aacgcacggt aaagtgggag      420
cccagcaccg agaacctgta cgtccgcgac ggagtcctga agggagacgt gaacatggcg      480
ctttcattgg aaggtggcgg gcactacaga tgcgatttca agacgaccta taaggcgaaa      540
aaggtggtcc aactgccgga ctaccatttc gtcgaccacc acatcgagat caagagccac      600
gacaaagact atagcaacgt gaatctccac gagcatgccg aggcccacag cgagctgccc      660
aggcaggcca ag                                                          672
```

<210> SEQ ID NO 5
<211> LENGTH: 224
<212> TYPE: PRT
<213> ORGANISM: Artificial
<220> FEATURE:
<223> OTHER INFORMATION: Padron-145N

<400> SEQUENCE: 5

```
Met Ser Val Ile Lys Pro Asp Met Lys Ile Lys Leu Arg Met Glu Gly
1               5                   10                  15

Ala Val Asn Gly His Pro Phe Ala Ile Glu Gly Val Gly Leu Gly Lys
            20                  25                  30

Pro Phe Glu Gly Lys Gln Ser Met Asp Leu Lys Val Lys Glu Gly Gly
        35                  40                  45

Pro Leu Pro Phe Ala Tyr Asp Ile Leu Thr Met Ala Phe Cys Tyr Gly
    50                  55                  60

Asn Arg Val Phe Ala Lys Tyr Pro Glu Asn Ile Val Asp Tyr Phe Lys
65                  70                  75                  80

Gln Ser Phe Pro Glu Gly Tyr Ser Trp Glu Arg Ser Met His Tyr Glu
                85                  90                  95

Asp Gly Gly Ser Cys Asn Ala Thr Asn Asp Ile Thr Leu Asp Gly Asp
            100                 105                 110

Cys Tyr Ile Tyr Glu Ile Arg Phe Asp Gly Val Asn Phe Pro Ala Asn
        115                 120                 125

Gly Pro Val Met Gln Lys Arg Thr Val Lys Trp Glu Arg Ser Thr Glu
    130                 135                 140

Asn Leu Tyr Val Arg Asp Gly Val Leu Lys Ser Asp Gly Asn Tyr Ala
145                 150                 155                 160

Leu Ser Leu Glu Gly Gly Gly His Tyr Arg Cys Asp Phe Lys Thr Thr
                165                 170                 175

Tyr Lys Ala Lys Lys Val Val Gln Leu Pro Asp Tyr His Ser Val Asp
            180                 185                 190

His His Ile Glu Ile Lys Ser His Asp Lys Asp Tyr Ser Asn Val Asn
        195                 200                 205

Leu His Glu His Ala Glu Ala His Ser Glu Leu Pro Arg Gln Ala Asn
    210                 215                 220
```

<210> SEQ ID NO 6
<211> LENGTH: 675
<212> TYPE: DNA
<213> ORGANISM: Artificial
<220> FEATURE:
<223> OTHER INFORMATION: Padron-145N

<400> SEQUENCE: 6

```
atgagtgtga ttaaaccaga catgaagatc aagctgcgta tggaaggcgc tgtaaatgga    60
cacccgttcg cgattgaagg agttggcctt gggaagcctt tcgagggaaa acagagtatg   120
gaccttaaag tcaaagaagg cggacctctg cctttcgcct atgacatctt gacaatggcg   180
ttctgttacg gcaacagggt attcgccaaa tacccagaaa atatagtaga ctatttcaag   240
cagtcgtttc ctgagggcta ctcttgggag cgaagcatgc attacgaaga cgggggctca   300
tgtaacgcga caaacgacat aaccctggat ggtgactgtt atatctatga aattcgattt   360
gatggcgtga actttcctgc caatggtcca gttatgcaga gaggactgt gaaatgggag    420 cggtccactg agaacttgta tgtgcgtgat ggagtgctga agtctgatgg taactacgct   480
ctgtcgcttg aaggaggtgg ccattaccga tgtgacttca aaactactta taaagctaag   540
aaggttgtcc agttgccaga ctatcactct gtggaccacc acattgagat taaaagccac   600
gacaaagatt acagtaatgt taatctgcat gagcatgccg aagcgcattc tgagctgccg   660
aggcaggcca actaa                                                    675
```

<210> SEQ ID NO 7
<211> LENGTH: 233
<212> TYPE: PRT
<213> ORGANISM: Artificial
<220> FEATURE:
<223> OTHER INFORMATION: rsTagRFP

<400> SEQUENCE: 7

Met Ser Glu Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Asn His Thr Gln Gly Ile Pro Asp Phe Trp
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Cys Leu Ile Tyr Asn Val Lys Leu Arg Gly Val Asn Phe Pro Ser
        115                 120                 125

Asn Gly Pro Val Met Gln Lys Lys Thr Leu Gly Trp Glu Ala Ala Thr
    130                 135                 140

Glu Met Leu Tyr Pro Ala Asp Gly Gly Leu Glu Gly Arg Gly Asp Met
145                 150                 155                 160

Ala Leu Lys Leu Val Gly Gly Gly His Leu Ile Cys Asn Leu Lys Thr
                165                 170                 175

Thr Tyr Arg Ser Lys Asn Pro Ala Lys Asn Leu Lys Met Pro Gly Val
            180                 185                 190

Tyr Phe Val Asp His Arg Leu Glu Arg Ile Lys Glu Ala Asp Lys Glu
        195                 200                 205

Thr Tyr Val Glu Gln His Glu Val Ala Val Ala Arg Tyr Cys Asp Leu
    210                 215                 220

Pro Ser Lys Leu Gly His Lys Leu Asn
225                 230

<210> SEQ ID NO 8
<211> LENGTH: 759
<212> TYPE: DNA
<213> ORGANISM: Artificial
<220> FEATURE:
<223> OTHER INFORMATION: rsTagRFP

<400> SEQUENCE: 8

```
atgagcgagc tgattaagga gaacatgcac atgaagctgt acatggaggg caccgtgaac      60
aaccaccact tcaagtgcac atccgagggc gaaggcaagc cctacgaggg cacccagacc     120
atgagaatca aggtggtcga gggcggccct ctccccttcg ccttcgacat cctggctacc     180
agcttcatgt acggcagccg caccttcatc aaccacaccc agggcatccc cgacttctgg     240
aagcagtcct tccctgaggg cttcacatgg gagagagtca ccacatacga agacgggggc     300
gtgctgaccg ctacccagga caccagcctc caggacggct gcctcatcta caacgtcaag     360
ctcagagggg tgaacttccc atccaacggc cctgtgatgc agaagaaaac actcggctgg     420
gaggccgcca ccgagatgct gtaccccgct gacgcggcc tggaaggcag aggggacatg      480
gccctgaagc tcgtgggcgg gggccacctg atctgcaact tgaagaccac atacagatcc     540
aagaatcccg ctaagaacct caagatgccc ggcgtctact ttgtggacca cagactggaa     600
agaatcaagg aggccgacaa agagacctac gtcgagcagc acgaggtggc tgtggccaga     660
tactgcgacc tccctagcaa actggggcac aagcttaatt aagaattcga agcttggctg     720
ttttggcgga tgagagaaga ttttcagcct gatacagat                             759
```

<210> SEQ ID NO 9
<211> LENGTH: 236
<212> TYPE: PRT
<213> ORGANISM: Artificial
<220> FEATURE:
<223> OTHER INFORMATION: mApple-162H-164A

<400> SEQUENCE: 9

```
Met Val Ser Lys Gly Glu Glu Asn Asn Met Ala Ile Ile Lys Glu Phe
1               5                   10                  15
Met Arg Phe Lys Val His Met Glu Gly Ser Val Asn Gly His Glu Phe
            20                  25                  30
Glu Ile Glu Gly Glu Gly Glu Gly Arg Pro Tyr Glu Ala Phe Gln Thr
        35                  40                  45
Ala Lys Leu Lys Val Thr Lys Gly Gly Pro Leu Pro Phe Ala Trp Asp
    50                  55                  60
Ile Leu Ser Pro Gln Phe Met Tyr Gly Ser Lys Val Tyr Ile Lys His
65                  70                  75                  80
Pro Ala Asp Ile Pro Asp Tyr Phe Lys Leu Ser Phe Pro Glu Gly Phe
                85                  90                  95
Arg Trp Glu Arg Val Met Asn Phe Glu Asp Gly Gly Ile Ile His Val
            100                 105                 110
Asn Gln Asp Ser Ser Leu Gln Asp Gly Val Phe Ile Tyr Lys Val Lys
        115                 120                 125
Leu Arg Gly Thr Asn Phe Pro Ser Asp Gly Pro Val Met Gln Lys Lys
    130                 135                 140
Thr Met Gly Trp Glu Ala Ser Glu Glu Arg Met Tyr Pro Glu Asp Gly
145                 150                 155                 160
Ala His Lys Ala Glu Ile Lys Lys Arg Leu Lys Leu Lys Asp Gly Gly
                165                 170                 175
His Tyr Ala Ala Glu Val Lys Thr Thr Tyr Lys Ala Lys Lys Pro Val
```

```
                    180                 185                 190
Gln Leu Pro Gly Ala Tyr Ile Val Asp Ile Lys Leu Asp Ile Val Ser
            195                 200                 205

His Asn Glu Asp Tyr Thr Ile Val Glu Gln Tyr Glu Arg Ala Glu Gly
            210                 215                 220

Arg His Ser Thr Gly Gly Met Asp Glu Leu Tyr Lys
225                 230                 235

<210> SEQ ID NO 10
<211> LENGTH: 708
<212> TYPE: DNA
<213> ORGANISM: Artificial
<220> FEATURE:
<223> OTHER INFORMATION: mApple-162H-164A

<400> SEQUENCE: 10
atggtgagca agggcgagga gaataacatg gccatcatca aggagttcat gcgcttcaag      60
gtgcacatgg agggctccgt gaacggccac gagttcgaga tcgagggcga gggcgagggc     120
cgcccctacg aggcctttca gaccgctaag ctgaaggtga ccaagggtgg ccccctgccc     180
ttcgcctggg acatcctgtc ccctcagttc atgtacggct ccaaggtcta cattaagcac     240
ccagccgaca tccccgacta cttcaagctg tccttccccg agggcttcag gtgggagcgc     300
gtgatgaact tcgaggacgg cggcattatt cacgttaacc aggactcctc cctgcaggac     360
ggcgtgttca tctacaaggt gaagctgcgc ggcaccaact cccctccga cggccccgta      420 atgcagaaga gaccatgggc ctgggaggcc tccgaggagc ggatgtaccc cgaggacggc     480
gcccataagt atgagatcaa gaagaggctg aagctgaagg acggcggcca ctacgccgcc     540
gaggtcaaga ccacctacaa ggccaagaag cccgtgcagc tgcccggcgc ctacatcgtc     600
gacatcaagt tggacatcgt gtcccacaac gaggactaca ccatcgtgga acagtacgaa     660
cgcgccgagg gccgccactc caccggcggc atggacgagc tgtacaag                 708

<210> SEQ ID NO 11
<211> LENGTH: 4
<212> TYPE: PRT
<213> ORGANISM: Artificial
<220> FEATURE:
<223> OTHER INFORMATION: linker

<400> SEQUENCE: 11

Gly Gly Ser Gly
1

<210> SEQ ID NO 12
<211> LENGTH: 5
<212> TYPE: PRT
<213> ORGANISM: Artificial
<220> FEATURE:
<223> OTHER INFORMATION: linker

<400> SEQUENCE: 12

Gly Gly Gly Gly Ser
1               5

<210> SEQ ID NO 13
<211> LENGTH: 4
<212> TYPE: PRT
<213> ORGANISM: Artificial
<220> FEATURE:
<223> OTHER INFORMATION: linker

<400> SEQUENCE: 13
```

Ser Ala Gly Gly
1

<210> SEQ ID NO 14
<211> LENGTH: 5
<212> TYPE: PRT
<213> ORGANISM: Artificial
<220> FEATURE:
<223> OTHER INFORMATION: nuclear localization signal

<400> SEQUENCE: 14

Lys Lys Lys Arg Lys
1               5

<210> SEQ ID NO 15
<211> LENGTH: 26
<212> TYPE: PRT
<213> ORGANISM: Artificial
<220> FEATURE:
<223> OTHER INFORMATION: mitochondrial localization sequence

<400> SEQUENCE: 15

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 16
<211> LENGTH: 4
<212> TYPE: PRT
<213> ORGANISM: Artificial
<220> FEATURE:
<223> OTHER INFORMATION: endoplasmic reticulum localization sequence

<400> SEQUENCE: 16

Lys Asp Glu Leu
1

<210> SEQ ID NO 17
<211> LENGTH: 4
<212> TYPE: PRT
<213> ORGANISM: Artificial
<220> FEATURE:
<223> OTHER INFORMATION: plasma membrane localization sequence
<220> FEATURE:
<221> NAME/KEY: misc_feature
<222> LOCATION: (2)..(3)
<223> OTHER INFORMATION: aliphatic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 17

Cys Xaa Xaa Xaa
1

<210> SEQ ID NO 18
<211> LENGTH: 4
<212> TYPE: PRT
<213> ORGANISM: Artificial
<220> FEATURE:
<223> OTHER INFORMATION: plasma membrane localization sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 18

```
Cys Cys Xaa Xaa
1

<210> SEQ ID NO 19
<211> LENGTH: 14
<212> TYPE: PRT
<213> ORGANISM: Homo sapiens

<400> SEQUENCE: 19

Lys Lys Lys Lys Lys Lys Ser Lys Thr Lys Cys Val Ile Met
1               5                  10

<210> SEQ ID NO 20
<211> LENGTH: 42
<212> TYPE: DNA
<213> ORGANISM: Homo sapiens

<400> SEQUENCE: 20
aagaagaaaa agaagaagtc caagactaag tgcgtgatca tg                          42

<210> SEQ ID NO 21
<211> LENGTH: 20
<212> TYPE: PRT
<213> ORGANISM: Homo sapiens

<400> SEQUENCE: 21

Lys Met Ser Lys Asp Gly Lys Lys Lys Lys Lys Ser Lys Thr Lys
1               5                  10                  15

Cys Val Ile Met
            20
```

OPTICAL CONTROL OF PROTEIN ACTIVITY AND LOCALIZATION BY FUSION TO PHOTOCHROMIC PROTEIN DOMAINS

CROSS-REFERENCE TO RELATED APPLICATION

This application claims benefit under 35 U.S.C. §119(e) of provisional application 61/614,492, filed Mar. 22, 2012, which application is hereby incorporated by reference in its entirety.

TECHNICAL FIELD

The present invention pertains generally to the field of protein engineering and methods of controlling the activity or cellular localization of proteins. In particular, the invention relates to engineered fusion proteins comprising photochromic protein domains and methods of using them to control protein activity or localization with light.

BACKGROUND

The ability to control protein localization and activity would be enormously beneficial for understanding and modulating protein function in physiological processes. Several approaches have been developed previously for optical control of protein activity using natural proteins and protein domains that change conformation upon light absorption, for example, using proteins such as rhodopsins, phytochromes, and cryptochromes, and LOV domains from phototropins and FKF1 (Airan et al. (2009) Nature 458:1025-1029; Inoue et al. (2005) Nat. Methods 2:415-418; Kennedy et al. (2010) Nat. Methods 7:973-975; Levskaya et al. (2009) Nature 461:997-1001; Szobota et al. (2007) Neuron 54:535-545; Wu et al. (2009) Nature 461:104-108; and Yazawa et al. (2009) Nat. Biotechnol. 27:941-945). However, widespread implementation of these methods has been hindered by various problems, including the limited applicability of the methods to only specific signaling pathways (Airan et al., supra), the need for exogenous cofactors (Levskaya et al., supra), slow kinetics of induction (Yazawa et al., supra), undesirable light-independent dimerization (Kennedy et al., supra), or the toxicity of light at blue wavelengths (Szobota et al., supra; Wu et al., supra; Yazawa et al., supra). Furthermore, of all these strategies, only fusion to LOV domains has been used to control the activity of a single protein, but this method generally requires extensive customization (Wu et al., supra; Strickland et al. (2008) Proc. Natl. Acad. Sci. U.S.A. 105:10709-10714; Strickland et al. (2010) Nat. Methods 7:623-626; and Wu et al. (2011) Methods Enzymol. 497:393-407). In addition, none of these light-absorbing domains are capable of controlling both protein localization by intermolecular interactions and function of a single polypeptide chain.

Thus, there remains a need for a simple to use system for controlling protein localization and activity with light, which can be readily applied to a wide range of proteins.

SUMMARY

The invention relates to engineered fusion proteins comprising photochromic protein domains. In particular, the inventors have constructed fusion proteins containing a photoswitchable photochromic fluorescent protein. The inventors have further shown that fusion proteins comprising one or more photochromic fluorescent protein domains linked to a selected protein of interest can be used to control the activity or localization of the selected protein using light.

In one aspect, the invention includes a fusion protein comprising at least one photochromic polypeptide connected to a selected polypeptide of interest, wherein the oligomerization state of the photochromic polypeptide is controllable with light. The photochromic polypeptide may be a photochromic protein, or a variant or polypeptide fragment thereof having fluorescence characteristics, wherein the fluorescence characteristics of the fusion protein are dependent on the oligomerization state of the photochromic polypeptide. For example, photochromic proteins including, but not limited to Dronpa, Padron, rsTagRFP, and mApple, or a variant or polypeptide fragment thereof having fluorescence characteristics (e.g., Dronpa-145N, Padron-145N, or mApple-162H-164A), may be used in fusion constructs. In certain embodiments, the fusion protein comprises at least one photochromic polypeptide comprising an amino acid sequence selected from the group consisting of SEQ ID NOS:1, 3, 5, 7, and 9 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto.

In certain embodiments, the fusion protein comprises at least two photochromic polypeptides, wherein a first photochromic polypeptide is connected to the N-terminus of the selected polypeptide of interest and a second photochromic polypeptide is connected to the C-terminus of the selected polypeptide of interest, wherein the oligomerization state of the first photochromic polypeptide and the second photochromic polypeptide is controllable with light. For example, the fusion protein may comprise two or more Dronpa, Padron, rsTagRFP, or mApple polypeptides. The photochromic polypeptides in the fusion protein can be the same or different.

In certain embodiments, the fusion protein comprises a Dronpa protein, or a variant or polypeptide fragment thereof having fluorescence and oligomerization characteristics. The fusion protein may comprise at least one Dronpa 145N or Dronpa 145 K polypeptide. In certain embodiments, the fusion protein comprises two Dronpa polypeptides, which can be the same or different. For example, the fusion protein may comprise two Dronpa 145N polypeptides, or two Dronpa 145K polypeptides, or a Dronpa 145K polypeptide and a Dronpa 145N polypeptide.

In certain embodiments, the fusion protein further comprises one or more linkers connecting polypeptides within the fusion protein. Linkers are typically short peptide sequences of 2-30 amino acid residues, often composed of glycine and/or serine residues. Linker sequences that can be used in the practice of the invention include, but are not limited to [Gly]$_x$, [Gly-Ser]$_x$, [Gly-Gly-Ser-Gly]$_x$, [Ser-Ala-Gly-Gly]$_x$, and [Gly-Gly-Gly-Gly-Ser]$_x$, wherein x=1-15, and GSAT, SEG, and Z-EGFR linkers.

In certain embodiments, the fusion protein further comprises a targeting sequence. Targeting sequences that can be used in the practice of the invention include, but are not limited to a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein-protein interaction motif sequence.

In certain embodiments, the fusion protein further comprises a tag. Tags that can be used in the practice of the invention include, but are not limited to a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

The fusion proteins described herein can be used to control the activity or localization of a selected protein, which may be a membrane protein, a receptor, a hormone, a transport protein, a transcription factor, a cytoskeletal protein, an extracellular matrix protein, a signal-transduction protein, an enzyme, or any other protein of interest. The fusion protein may comprise the entire protein, or a biologically active domain (e.g., a catalytic domain, a ligand binding domain, or a protein-protein interaction domain), or a polypeptide fragment of the selected protein of interest.

In another aspect, the invention includes a method for controlling the activity of a selected polypeptide of interest with light. The method comprises (i) preparing a fusion protein comprising a first photochromic polypeptide connected to the N-terminus of the selected polypeptide of interest and a second photochromic polypeptide connected to the C-terminus of the selected polypeptide of interest; (ii) illuminating the fusion protein with light at a wavelength that induces intramolecular dimerization of the first photochromic polypeptide and the second photochromic polypeptide (e.g., about 405 nm for some fusions with Dronpa 145N or 145K), such that the activity of the selected polypeptide of interest is inactivated. In certain embodiments, the method further comprises illuminating the fusion protein with light at a wavelength that induces dissociation of the first photochromic polypeptide from the second photochromic polypeptide (e.g., about 480-500 nm for some fusions with Dronpa 145N or 145K), such that the activity of the selected polypeptide is restored. Localization of the selected polypeptide as well as inactivation of the selected polypeptide can be visualized by detecting fluorescence of the fusion protein resulting from intramolecular dimerization of the first photochromic polypeptide and the second photochromic polypeptide in the fusion protein. Inactivation of the selected polypeptide can further be assessed by measuring the activity of the selected polypeptide.

In another aspect, the invention includes a method for controlling the localization of a selected polypeptide of interest with light. The method comprises (i) preparing a first fusion protein comprising a photochromic polypeptide connected to a targeting sequence; (ii) preparing a second fusion protein comprising a photochromic polypeptide connected to the selected polypeptide of interest; (iii) introducing the first fusion protein and the second fusion protein into a cell, wherein the localization sequence targets the first fusion protein to a particular subcellular location; (iv) and illuminating the fusion proteins with light at a wavelength that induces oligomerization of the photochromic polypeptide in the first fusion protein with the photochromic polypeptide in the second fusion protein (e.g., about 405 nm for some fusions with Dronpa 145N or 145K), such that the selected polypeptide of interest accumulates at the subcellular location. In certain embodiments, the method further comprises illuminating the fusion proteins with light at a wavelength that induces dissociation of the photochromic polypeptides (e.g., about 480-500 nm for some fusions with Dronpa 145N or 145K), such that the selected polypeptide in the second fusion protein is released from the subcellular location. Localization of the selected polypeptide can be visualized by detecting fluorescence of the fusion proteins resulting from the oligomerization of the photochromic polypeptides.

In another aspect, the invention includes a method for controlling the localization of a selected polypeptide of interest with light. The method comprises: (i) preparing a fusion protein comprising a photochromic polypeptide, a targeting sequence, and the selected polypeptide of interest; (ii) introducing the fusion protein into a cell, wherein the localization sequence targets the fusion protein to a particular subcellular location; and (iii) illuminating the fusion protein with light at a wavelength that induces oligomerization of the photochromic polypeptide in the fusion protein with photochromic polypeptides in other fusion proteins (e.g., 405 nm for some fusions with Dronpa 145N or 145K), the other fusion proteins comprising the selected polypeptide, such that the selected polypeptide accumulates at the subcellular location. In certain embodiments, the method further comprises illuminating the fusion protein with light at a wavelength that induces dissociation of the photochromic polypeptides (e.g, about 480-500 nm for some fusions with Dronpa 145N or 145K), such that the selected polypeptide in the fusion protein is released from the subcellular location. Localization of the selected polypeptide can be visualized by detecting fluorescence of the fusion protein resulting from the oligomerization with photochromic polypeptides of the other fusion proteins.

In another aspect, the invention includes a polynucleotide encoding a fusion protein described herein. In one embodiment, the polynucleotide is a recombinant polynucleotide comprising a polynucleotide encoding a fusion protein operably linked to a promoter. In certain embodiments, the recombinant polynucleotide comprises a polynucleotide selected from the group consisting of: a polynucleotide encoding a polypeptide comprising a sequence selected from the group consisting of SEQ ID NOS:1, 3, 5, 7, and 9; a polynucleotide encoding a polypeptide comprising a sequence having at least 95% identity to a sequence selected from the group consisting of SEQ ID NOS:1, 3, 5, 7, and 9; a polynucleotide comprising a sequence selected from the group consisting of SEQ ID NOS:2, 4, 6, 8, and 10; and a polynucleotide comprising a sequence having at least 95% identity to a sequence selected from the group consisting of SEQ ID NOS:2, 4, 6, 8, and 10.

In another aspect, the invention includes a host cell comprising a recombinant polynucleotide encoding a fusion protein operably linked to a promoter.

In another aspect, the invention includes a method for producing a fusion protein, the method comprising: transforming a host cell with a recombinant polynucleotide encoding a fusion protein operably linked to a promoter; culturing the transformed host cell under conditions whereby the fusion protein is expressed; and isolating the fusion protein from the host cell.

In another aspect, the invention includes a kit for preparing or using fusion proteins according to the methods described herein. Such kits may comprise one or more photochromic polypeptides or fusion proteins, or nucleic acids encoding such polypeptides or fusion proteins, or expression vectors, or cells, or other reagents for preparing polypeptides and fusion proteins, as described herein.

In the practice of the invention, the fluorescence of fusion proteins can be monitored by any suitable method. For example, fluorescence of fusion proteins can be detected by a fluorometer, a fluorescence microscope, a fluorescence microplate reader, a fluorometric imaging plate reader, or fluorescence-activated cell sorting.

These and other embodiments of the subject invention will readily occur to those of skill in the art in view of the disclosure herein.

BRIEF DESCRIPTION OF THE FIGURES

FIG. 1A shows a schematic representation of the hypothesized bidirectional control of the Dronpa145N oligomerization state by 500-nm cyan and 400-nm violet light. FIG. 1B shows native polyacrylamide gel electrophoresis (PAGE) of Dronpa145N (100 µM), which demonstrated that 500 nm light induced dissociation and 400 nm light induced retetramerization. The mRuby2 (Lam et al. (2012) Nat. Methods 9:1005-1012), tdTomato, and dsRed2 (20 µM) served as monomeric, dimeric, and tetrameric standards, respectively. All proteins were polyhistidine-tagged at the amino terminus (NT). FIG. 1C shows absorbance spectra confirming that photoswitching is reversible. FIG. 1D shows a schematic representation of the hypothesized bidirectional conformational switching by light in a Dronpa145K-Dronpa145N (K-N) tandem dimer. FIG. 1E shows that native PAGE of the K-N tandem dimer demonstrated faster migration by the K-N tandem dimer (100 µM) after exposure to 500-nm light, an effect that was reversed by 400-nm light. The asterisk marks the location expected for tandem dimer migration, similar to tdTomato. Some cleavage of the tandem dimer to a monomer in this protein preparation was apparent. FIG. 1F shows absorbance spectra of K-N tandem dimers confirming that photoswitching is reversible.

FIG. 2A shows the experimental plan for light-regulated interaction between Dronpa145N-CAAX (N-CAAX) and mNeptune-Dronpa145N (mNeptune-N). FIG. 2B shows quantitation of membrane Dronpa fluorescence during 490/20-nm illumination. FIG. 2C shows that 490/20-nm light induced off-photoswitching of Dronpa and loss of mNeptune from the plasma membrane (scale bar, 20 µm). FIG. 2D shows an intensity profile for the region between the arrows shown in FIG. 2C. FIG. 2E shows the experimental plan for light-regulated interaction between Dronpa145K-CAAX (K-CAAX) and mNeptune-N. FIG. 2F shows the quantitation of membrane Dronpa fluorescence during 490/20-nm illumination. FIG. 2G shows that 490/20-nm light induced off-photoswitching of Dronpa and loss of mNeptune from the membrane. mNeptune reappeared at the membrane after 3-seconds of on-photoswitching with 390/15-nm light (scale bar, 20 µm). FIG. 2H shows intensity profiles for the region between the arrows shown in FIG. 2G.

FIG. 3A shows the proposed mechanism for photo-uncaging of N-I-N-CAAX activity (construct contained Dronpa145N at the N-terminus of the intersectin (ITSN) Dbl homology (DH) domain and Dronpa145N at the C-terminus followed by the CAAX sequence). FIG. 3B shows off-photoswitching of Dronpa fluorescence in N-I-N-CAAX versus 490/20-nm light dosage during microscopy. Whole-cell fluorescence results from five cells were quantified and normalized to the initial value. Error bars represent standard deviation (SD). FIG. 3C shows that in NIH 3T3 cells expressing N-I-N-CAAX, 490/20-nm illumination for 30 seconds (off-switching) followed by incubation at 37° C. for 30 minutes resulted in robust induction of filopodia, as revealed by mNeptune-Fascin. FIG. 3D shows that local illumination by 490/20-nm light locally induced filopodia, marked by mNeptune-fascin, in NIH 3T3 cells expressing N-I-N-CAAX. The dotted curves indicate the area of illumination. FIG. 3E shows the proposed mechanism for photo-uncaging of K-I-N-CAAX activity (construct contained Dronpa145K at the N-terminus of the intersectin (ITSN) Dbl homology (DH) domain and Dronpa145N at the C-terminus followed by the CAAX sequence). FIG. 3F shows off-photoswitching of Dronpa fluorescence in K-I-N-CAAX versus 490/20-nm light dosage during microscopy. The experiment was performed as described for FIG. 3B. FIG. 3G shows that in NIH 3T3 cells expressing K-I-N-CAAX, exposure to 490/20-nm light for 30 seconds (off-switching) followed by incubation at 37° C. for 30 minutes resulted in robust induction of filopodia. FIG. 3H shows that local illumination by 490/20-nm light locally induced filopodia, marked by mNeptune-fascin, in NIH 3T3 cells expressing K-I-N-CAAX. The dotted curves indicate the area of illumination. The scale bars in FIGS. 3C, 3D, 3G, and 3H are 20 µm.

FIG. 4A shows the strategy for sensing activity of the N-protease-N protein with mCherry-substrate-CAAX. FIG. 4B shows the distribution of mCherry in cells expressing mCherry-substrate-CAAX in the absence (left) or presence (middle) of cotransfected K-protease. The chart at right shows the fluorescence intensity profile along the line between the arrows in the images. FIG. 4C shows that as expected from its size (81 kD), N-protease-N was excluded from the nucleus (left). Exposure to 490/20-nm light for 15 seconds induced off-photoswitching of Dronpa fluorescence (Dronpa channel) and induced release of mCherry from the membrane (mCherry channel). The chart at right shows the intensity profile along the line between the arrows in the images, which confirmed that mCherry fluorescence decreases from the membrane and increases in the cytosol and nucleus after illumination. The scale bars in FIGS. 4B and 4C are 20 µm.

FIG. 5A shows a native PAGE, which demonstrated that Dronpa145K is purely monomeric and 145N is predominantly tetrameric at concentrations from 10 µM to 100 µM. The mRuby2, tdTomato, and dsRed2 served as monomeric, dimeric, and tetrameric standards, respectively. FIG. 5B shows that fluorescence of Dronpa145N was switched off by 500 nm light and switched back on by 400 nm light using the same conditions as described for FIG. 1. Fluorescence was measured in quadruplicate at 480/5 nm excitation and 530/5 nm emission and intensities normalized to the initial value. Error bars represent standard deviation. FIG. 5C shows that fluorescence of the Dronpa145K-Dronpa145N tandem dimer was switched off by 500 nm light and switched back on by 400 nm light using the same conditions as described for FIG. 1.

FIG. 6A shows that N-CAAX did not recruit mNeptune-K to the membrane, possibly due to N-N intramembrane homotetramerization outcompeting K-N heterodimerization. FIG. 6B shows that K-CAAX was unable to recruit mNeptune-K to the membrane, confirming mNeptune membrane localization required Dronpa multimerization. Scale bars are 10 µm.

FIGS. 7A-7D show protein caging by fusion to interacting FP domains. FIG. 7A shows structural models of a DH domain caged by two flanking Dronpa145N domains (top), or flanking Dronpa145K and Dronpa145N domains (bottom). FIG. 7B shows the organization of the control intersectin Dbl-homology domain (ITSN DH) constructs, caged ITSN DH constructs, and a mNeptune-fascin filopodia reporter. FIG. 7C shows representative NIH 3T3 fibroblasts expressing K-CAAX, K-I-CAAX, I-K-CAAX, N-I-N-CAAX, or K-I-N-CAAX (Dronpa channel) with filopodia and lamellipodia marked by mNeptune-fascin (mNeptune channel). The scale bar is 10 µm. FIG. 7D shows the frequency of filopodia or lamellipodia formation in cells transiently transfected with various constructs. Cells showing lamellipodia or more than one filopodium at one polygonal side were scored as positive. Numbers above the bars are the number of cells in each condition. All imaged cells were scored. The scale bars are 10 µm.

FIG. 8A shows the distribution of Dronpa fluorescence intensities from 37 cells transfected with N-I-N-CAAX. Boundaries for defining low, medium, and high expressers are shown as dotted lines. FIG. 8B shows the occurrence of filopodia or lamellipodia is low in cells expressing low levels of N-I-N-CAAX. FIG. 8C shows the distribution of Dronpa fluorescence intensities from 50 cells transfected with K-I-N-CAAX. Boundaries for defining low, medium, and high expressers are shown as dotted lines. FIG. 8D shows that the occurrence of filopodia or lamellipodia is low in cells expressing low levels of K-I-N-CAAX.

FIG. 9A shows that cells expressing N-I-N-CAAX did not produce filopodia without illumination. Initial Dronpa was not imaged to avoid uncaging by the 500 nm excitation light. FIG. 9B shows that cells expressing K-I-N-CAAX did not produce filopodia under identical conditions without illumination. Initial Dronpa was not imaged to avoid uncaging by the 490/20 nm excitation light. FIG. 9C shows that in cells expressing K-CAAX (lacking ITSN DH), 490/20 nm illumination for 30 seconds (Dronpa off-switching) followed by incubation at 37° C. for 30 minutes did not produce filopodia or lamellipodia. FIG. 9D shows that quantitation of new filopodia and lamellipodia formation with light stimulation in cells expressing N-I-N-CAAX and K-I-N-CAAX. Numbers above the bars are the number of cells in each condition. All imaged cells were scored. The scale bars are 10 µm.

FIG. 12A shows that HEK293 cells expressing mCherry-substrate-CAAX together with N-protease-N did not release mCherry from the membrane in the absence of light stimulation. FIG. 12B shows that cells expressing mCherry-substrate-CAAX alone did not release mCherry from the membrane even after light stimulation. Scale bars are 10 µm.

DETAILED DESCRIPTION

Figure 1A:
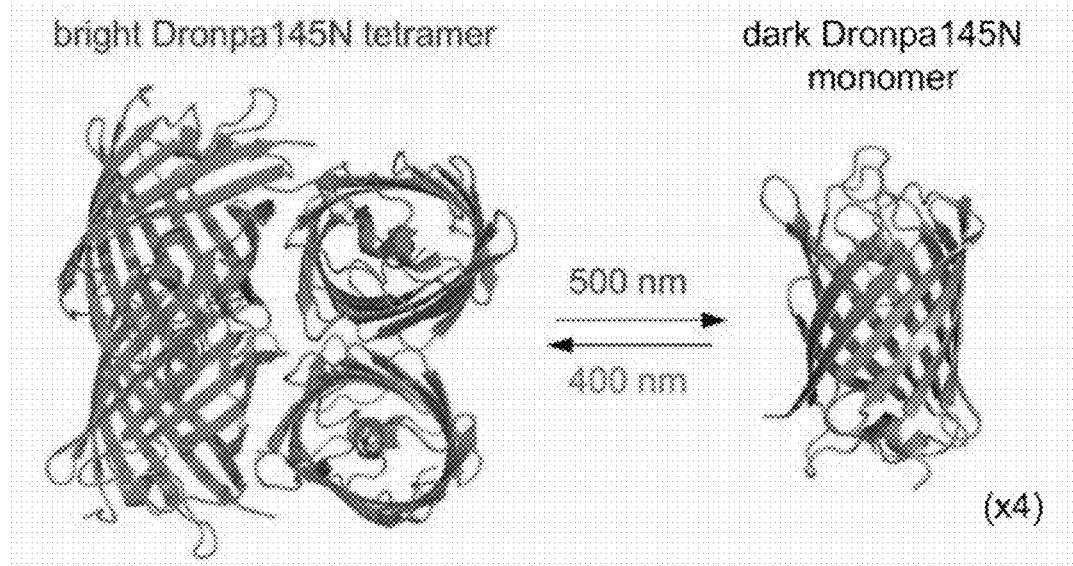
FIGS. 1A-1F show the control of photochromic fluorescent protein (FP) domain association by light.

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Handbook of Experimental Immunology*, Vols. I-IV (D. M. Weir and C. C. Blackwell eds., Blackwell Scientific Publications); A. L. Lehninger, Biochemistry (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a fusion protein" includes a mixture of two or more fusion proteins, and the like.

The term "about," particularly in reference to a given quantity, is meant to encompass deviations of plus or minus five percent.

"Fluorescent protein" refers to any protein capable of emitting light when excited with appropriate electromagnetic radiation. Fluorescent proteins include proteins having amino acid sequences that are either natural or engineered (e.g., Dronpa, Padron, rsTagRFP, and mApple, and variants and derivatives thereof).

A Dronpa polynucleotide, nucleic acid, oligonucleotide, protein, polypeptide, or peptide refers to a molecule derived from a coral of the genus *Pectimidae*. The molecule need not be physically derived from *Pectimidae*, but may be synthetically or recombinantly produced. A number of Dronpa nucleic acid and protein sequences are known. Representative Dronpa sequences are presented in SEQ ID NOS:1-4. Additional representative sequences are listed in the National Center for Biotechnology Information (NCBI) database. See, for example, NCBI entries: Accession Nos. AB180726, ADE48854, BAD72874.1, 2IOV_D, 2IOV_C, 2IOV_B, 2IOV_A, 2PDX_D, 2PDX_C, 2PDX_B, 2PDX_A, AED56657, AED56658, AED56659, and AED56660; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

A Padron polynucleotide, nucleic acid, oligonucleotide, protein, polypeptide, or peptide refers to a molecule derived from *Echinophyllia* sp. SC22. The molecule need not be physically derived from *Echinophyllia* sp., but may be synthetically or recombinantly produced. A number of Padron nucleic acid and protein sequences are known. Representative Padron sequences are presented in SEQ ID NO:5 and SEQ ID NO:6. Additional representative sequences are listed in the National Center for Biotechnology Information (NCBI) database. See, for example, NCBI entries: Accession Nos. ACL36360, ACL98050, EU983551, FJ014613, 3ZUL_A, 3ZUL_B, 3ZUL_C, 3ZUL_D, 3ZUL_E, 3ZUL_F, 3ZUJ_A, 3ZUJ_B, 3ZUJ_C, 3ZUJ_D, 3ZUJ_E, 3ZUJ_F, 3ZUF_A, 3ZUF_B, 3ZUF_C, 3ZUF_D, 3ZUF_E, and 3ZUF_F; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

An rsTagRFP polynucleotide, nucleic acid, oligonucleotide, protein, polypeptide, or peptide refers to a molecule derived from *Entacmaea quadricolor*. The molecule need not be physically derived from *Entacmaea quadricolor*, but may be synthetically or recombinantly produced. A number of rsTagRFP nucleic acid and protein sequences are known. Representative rsTagRFP sequences are presented in SEQ ID NO:7 and SEQ ID NO:8. Additional representative sequences are listed in the National Center for Biotechnology Information (NCBI) database. See, for example, NCBI entries: Accession Nos. 3U8C_A, 3U8C_B, 3U8C_C, 3U8C_D, 3U8A_A, 3U8A_B, 3U8A_C, 3U8A_D; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

An mApple polynucleotide, nucleic acid, oligonucleotide, protein, polypeptide, or peptide refers to a molecule derived from *Discosoma* sp. The molecule need not be physically derived from *Discosoma* sp., but may be synthetically or recombinantly produced. A number of mApple nucleic acid and protein sequences are known. Representative mApple sequences are presented in SEQ ID NO:9 and SEQ ID NO:10. Additional representative sequences are listed in the National Center for Biotechnology Information (NCBI) database. See, for example, NCBI entries: Accession Nos. ABC66097, DQ336160; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

The terms "fusion protein," "fusion polypeptide," or "photochromic fusion protein" as used herein refer to a fusion comprising at least one photochromic polypeptide in combination with a selected polypeptide of interest as part of a single continuous chain of amino acids, which chain does not occur in nature. The photochromic polypeptides and other selected polypeptides may be connected directly to each other by peptide bonds or may be separated by intervening amino acid sequences. The fusion may include entire proteins or fragments thereof, including, for example, sequences of Dronpa, Padron, rsTagRFP, mApple, or variants thereof having fluorescence characteristics (e.g., Dronpa-145K, Dronpa-145N, Padron-145N, and mApple-162H-164A). The fusion polypeptides may also contain sequences exogenous to the photochromic or other selected polypeptides. For example, the fusion may include targeting or localization sequences, tag sequences, sequences of other fluorescent proteins (e.g., other proteins with fluorescence characteristics that differ from Dronpa, Padron, rsTagRFP, or mApple), or other chromophores. Moreover, the fusion may contain sequences from multiple photochromic proteins, or variants thereof, and/or other selected proteins. For example, the fusion protein may comprise two or more Dronpa, Padron, rsTagRFP, or mApple polypeptides, which can be the same or different (e.g., two or more Dronpa 145K or Dronpa 145N polypeptides, or a Dronpa 145K polypeptide and a Dronpa 145N polypeptide simultaneously in the same fusion). Alternatively, the fusion protein may comprise only one photochromic polypeptide, which can be a wild-type polypeptide, or variant thereof.

The term "fluorescence characteristics" means an ability to emit fluorescence by irradiation of excitation light. The fluorescence characteristics of a fluorescent fusion protein comprising a photochromic polypeptide or a variant thereof may be comparable to or different from those of the fluorescent proteins which have the amino acid sequences shown in SEQ ID NOS:1, 3, 5, 7, and 9. Examples of parameters of the fluorescence characteristics include fluorescence intensity, excitation wavelength, fluorescence wavelength, and pH sensitivity.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, fluorescence or oligomerization characteristics, as defined herein.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. The term also includes fluorescent proteins and polypeptides.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80% 85% sequence identity, more preferably at least about 90% sequence identity, and most preferably at least about 95% 98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant," "analog" and "mutein" refer to biologically active derivatives of the reference molecule that retain desired activity, such as fluorescence or oligomerization characteristics. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of engineered fusion proteins comprising photochromic fluorescent protein domains that can be used to control the activity or localization of a selected protein of interest. In particular, the inventors have constructed fusion proteins containing photoswitchable variants of the fluorescent protein Dronpa (see Example 1). Dronpa undergoes light-inducible oligomerization, which converts Dronpa from a dark form to a bright form with detectable fluorescence. Thus, fusions of Dronpa with a selected protein allow the protein to be detected when Dronpa is converted to its bright form. The inventors have further shown that fusion proteins comprising Dronpa linked to a selected protein of interest can be used to control the activity or localization of the selected protein with light (see Example 1). In order to further an understanding of the invention, a more detailed discussion is provided below regarding photochromic fusion proteins and methods of using them to control the activity and localization of proteins.

A. Fusion Proteins

Fusion proteins comprise at least one photochromic polypeptide connected to a selected polypeptide of interest. The fusion protein can be designed to block or induce activity of the selected polypeptide of interest, control its interactions with other macromolecules, or direct its subcellular localization. The polypeptide of interest selected for study may be from a membrane protein, a receptor, a hormone, a transport protein, a transcription factor, a cytoskeletal protein, an extracellular matrix protein, a signal-transduction protein, an enzyme, or any other protein of interest. The fusion protein may include entire photochromic proteins, or biologically active domains or polypeptide fragments, or variants thereof having fluorescence characteristics (e.g., Dronpa-145K, Dronpa-145N, Padron-145N, rsTagRFP, and mApple-162H-164A). In addition, the fusion protein may comprise an entire selected protein of interest, or a biologically active domain (e.g., a catalytic domain, a ligand binding domain, or a protein-protein interaction domain), or a polypeptide fragment of the selected protein of interest.

Dronpa nucleic acid and protein sequences may be derived from corals of the genus *Pectimidae*. A number of Dronpa nucleic acid and protein sequences are known. Representative Dronpa sequences are presented in SEQ ID NOS:1-4 and additional representative sequences are listed in the National Center for Biotechnology Information (NCBI) database. See, for example, NCBI entries: Accession Nos. AB180726, ADE48854, BAD72874.1, 2IOV_D, 2IOV_C, 2IOV_B, 2IOV_A, 2PDX_D, 2PDX_C, 2PDX_B, 2PDX_A, AED56657, AED56658, AED56659, and AED56660; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

Padron nucleic acid and protein sequences may be derived from *Echinophyllia* sp. SC22. A number of Padron nucleic acid and protein sequences are known. Representative Padron sequences are presented in SEQ ID NO:5 and SEQ ID NO:6. Additional representative sequences are listed in the National Center for Biotechnology Information (NCBI) database. See, for example, NCBI entries: Accession Nos. ACL36360, ACL98050, EU983551, FJ014613, 3ZUL_A, 3ZUL_B, 3ZUL_C, 3ZUL_D, 3ZUL_E, 3ZUL_F, 3ZUJ_A, 3ZUJ_B, 3ZUJ_C, 3ZUJ_D, 3ZUJ_E, 3ZUJ_F, 3ZUF_A, 3ZUF_B, 3ZUF_C, 3ZUF_D, 3ZUF_E, and 3ZUF_F; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

RsTagRFP nucleic acid and protein sequences may be derived from *Discosoma* sp. A number of rsTagRFP nucleic acid and protein sequences are known. Representative rsTagRFP sequences are presented in SEQ ID NO:7 and SEQ ID NO:8. Additional representative sequences are listed in the National Center for Biotechnology Information (NCBI) database. See, for example, NCBI entries: Accession Nos. 3U8C_A, 3U8C_B, 3U8C_C, 3U8C_D, 3U8A_A, 3U8A_B, 3U8A_C, 3U8A_D; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

MApple nucleic acid and protein sequences may be derived from *Discosoma* sp. A number of mApple nucleic acid and protein sequences are known. Representative mApple sequences are presented in SEQ ID NO:9 and SEQ ID NO:10. Additional representative sequences are listed in the National Center for Biotechnology Information (NCBI)

database. See, for example, NCBI entries: Accession Nos. ABC66097, DQ336160; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fusion protein, as described herein.

The photochromic polypeptides and other polypeptides included in the fusion construct may be connected directly to each other by peptide bonds or may be separated by intervening amino acid sequences. The fusion polypeptides may also contain sequences exogenous to the photochromic polypeptides or the selected protein of interest. For example, the fusion may include targeting or localization sequences, tag sequences, sequences of other fluorescent proteins (e.g., with fluorescence characteristics that differ from other photochromic proteins in the fusion protein), or other chromophores. Moreover, the fusion may contain sequences from multiple photochromic proteins, or variants thereof, and/or non-photochromic proteins. For example, the fusion protein may comprise two or more photochromic polypeptides, which can be the same or different (e.g., two or more Dronpa 145K or Dronpa 145N polypeptides, or a Dronpa 145K polypeptide and a Dronpa 145N polypeptide simultaneously in the same fusion). Alternatively, the fusion protein may comprise only one photochromic polypeptide, which can be a wild-type photochromic polypeptide, or a variant thereof.

In certain embodiments, the fusion protein can be represented by the formula $NH_2$-A-D-L-X-B-COOH or $NH_2$-A-X-L-D-B-COOH, wherein: D is an amino acid sequence of a photochromic protein or a variant or polypeptide fragment thereof; L is an optional linker amino acid sequence; X is an amino acid sequence of a selected polypeptide of interest; A is an optional N-terminal amino acid sequence; and B is an optional C-terminal amino acid sequence.

In other embodiments, the fusion protein can be represented by the formula $NH_2$-A-$D_1$-L-X-L-$D_2$-B-COOH, wherein: $D_1$ and $D_2$ are amino acid sequences of a photochromic protein or a variant or polypeptide fragment thereof; L is an optional linker amino acid sequence; X is an amino acid sequence of a selected polypeptide of interest; A is an optional N-terminal amino acid sequence; and B is an optional C-terminal amino acid sequence. In fusion proteins comprising two photochromic polypeptides, the photochromic polypeptides $D_1$ and $D_2$ can be the same or different. For example, the fusion protein may comprise two Dronpa 145N polypeptides, or two Dronpa 145K polypeptides, or a Dronpa 145K polypeptide and a Dronpa 145N polypeptide. Where more than one linker is present in the fusion, the linkers can also be the same or different.

Linker amino acid sequence(s)-L- will typically be short, e.g., 20 or fewer amino acids (i.e., 20, 19, 18, 17, 16, 15, 14, 13, 12, 11, 10, 9, 8, 7, 6, 5, 4, 3, 2, or 1). Examples include short peptide sequences which facilitate cloning, poly-glycine linkers ($Gly_n$ where n=2, 3, 4, 5, 6, 7, 8, 9, 10 or more), histidine tags ($His_n$ where n=3, 4, 5, 6, 7, 8, 9, 10 or more), linkers composed of glycine and serine residues ([Gly-Ser]$_n$, [Gly-Gly-Ser-Gly]$_n$ (SEQ ID NO:11), [Gly-Gly-Gly-Gly-Ser]$_n$ (SEQ ID NO:12), and [Ser-Ala-Gly-Gly]$_n$ (SEQ ID NO:13), wherein n=1, 2, 3, 4, 5, 6, 7, 8, 9, 10, 11, 12, 13, 14, 15 or more), GSAT, SEG, and Z-EGFR linkers. Linkers may include restriction sites, which aid cloning and manipulation. Other suitable linker amino acid sequences will be apparent to those skilled in the art. (See e.g., Argos (1990) J. Mol. Biol. 211(4):943-958; Crasto et al. (2000) Protein Eng. 13:309-312; George et al. (2002) Protein Eng. 15:871-879; Arai et al. (2001) Protein Eng. 14:529-532; and the Registry of Standard Biological Parts (partsregistry.org/Protein domains/Linker).

-A- is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1). Examples include leader sequences to direct protein localization, or short peptide sequences or tag sequences, which facilitate cloning or purification (e.g., a histidine tag $His_n$ where n=3, 4, 5, 6, 7, 8, 9, 10 or more). Other suitable N-terminal amino acid sequences will be apparent to those skilled in the art.

-B- is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1). Examples include sequences to direct protein localization, short peptide sequences or tag sequences, which facilitate cloning or purification (e.g., $His_n$ where n=3, 4, 5, 6, 7, 8, 9, or more), or sequences which enhance protein stability. Other suitable C-terminal amino acid sequences will be apparent to those skilled in the art.

In certain embodiments, tag sequences are located at the N-terminus or C-terminus of the fusion protein. Exemplary tags that can be used in the practice of the invention include a His-tag, a Strep-tag, a TAP-tag, an S-tag, an SBP-tag, an Arg-tag, a calmodulin-binding peptide tag, a cellulose-binding domain tag, a DsbA tag, a c-myc tag, a glutathione S-transferase tag, a FLAG tag, a HAT-tag, a maltose-binding protein tag, a NusA tag, and a thioredoxin tag.

In certain embodiments, the fusion protein comprises a targeting sequence. Exemplary targeting sequences that can be used in the practice of the invention include a secretory protein signal sequence, a membrane protein signal sequence, a nuclear localization sequence, a nucleolar localization signal sequence, an endoplasmic reticulum localization sequence, a peroxisome localization sequence, a mitochondrial localization sequence, and a protein-protein interaction motif sequence. Examples of targeting sequences include those targeting the nucleus (e.g., KKKRK, SEQ ID NO:14), mitochondrion (e.g., MLRTSSLFTRRVQPSLFRNILRLQST, SEQ ID NO:15), endoplasmic reticulum (e.g., KDEL, SEQ ID NO:16), peroxisome (e.g., SKL), synapses (e.g., S/TDV or fusion to GAP 43, kinesin or tau), plasma membrane (e.g., CaaX (SEQ ID NO:17) where "a" is an aliphatic amino acid, CC, CXC, CCXX (SEQ ID NO:18) at C-terminus), or protein-protein interaction motifs (e.g., SH2, SH3, PDZ, WW, RGD, Src homology domain, DNA-binding domain, SLiMs).

In another aspect, the invention includes a method for controlling the activity of a selected polypeptide of interest with light. The method comprises (i) preparing a fusion protein comprising a first photochromic polypeptide connected to the N-terminus of the selected polypeptide of interest and a second photochromic polypeptide connected to the C-terminus of the selected polypeptide of interest; (ii) illuminating the fusion protein with light at a wavelength that induces intramolecular dimerization of the first photochromic polypeptide and the second photochromic polypeptide (e.g., about 405 nm for some fusions with Dronpa 145N or 145K), such that the activity of the selected polypeptide of interest is inactivated. In certain embodiments, the method further comprises illuminating the fusion protein with light that induces dissociation of the first photochromic polypeptide from the second photochromic polypeptide (e.g., about 480-500 nm for some fusions with Dronpa 145N or 145K), such that the activity of the selected polypeptide is restored. Localization of the selected polypeptide as well as inactivation of the selected polypeptide can be visualized by detecting fluorescence of the fusion protein resulting from intramolecular dimerization of the first photochromic polypeptide and the second photochromic polypeptide in the fusion protein. Inactivation of the selected polypeptide can further be assessed by measuring the activity of the selected polypeptide.

In another aspect, the invention includes a method for controlling the localization of a selected polypeptide of interest with light. The method comprises (i) preparing a first fusion protein comprising a photochromic polypeptide connected to a targeting sequence; (ii) preparing a second fusion protein comprising a photochromic polypeptide connected to the selected polypeptide of interest; (iii) introducing the first photochromic fusion and the second fusion protein into a cell, wherein the localization sequence targets the first fusion protein to a particular subcellular location; (iv) and illuminating the fusion proteins with light at a wavelength that induces oligomerization of the photochromic polypeptide in the first fusion protein with the photochromic polypeptide in the second fusion protein (e.g., about 405 nm for some fusions with Dronpa 145N or 145K), such that the selected polypeptide of interest accumulates at the subcellular location. In certain embodiments, the method further comprises illuminating the fusion proteins with light that induces dissociation of the photochromic polypeptides (e.g., about 480-500 nm for some fusions with Dronpa 145N or 145K), such that the selected polypeptide of interest in the second fusion protein is released from the subcellular location. Localization of the selected polypeptide of interest can be visualized by detecting fluorescence of the fusion proteins resulting from the oligomerization of the photochromic polypeptides.

In another aspect, the invention includes a method for controlling the localization of a selected polypeptide of interest with light. The method comprises: (i) preparing a fusion protein comprising a photochromic polypeptide, a targeting sequence, and the selected polypeptide of interest; (ii) introducing the fusion protein into a cell, wherein the localization sequence targets the fusion protein to a particular subcellular location; and (iii) illuminating the fusion protein with light at a wavelength that induces oligomerization of the photochromic polypeptide in the fusion protein with photochromic polypeptides in other fusion proteins (e.g., about 405 nm for some fusions with Dronpa 145N or 145K), said other fusion proteins comprising the selected polypeptide of interest, such that the selected polypeptide of interest accumulates at the subcellular location. In certain embodiments, the method further comprises illuminating the fusion protein with light at a wavelength that induces dissociation of the photochromic polypeptides (e.g., about 480-500 nm for some fusions with Dronpa 145N or 145K), such that the selected polypeptide of interest in the fusion protein is released from the subcellular location. Localization of the selected polypeptide of interest can be visualized by detecting fluorescence of the fusion protein resulting from the oligomerization with photochromic polypeptides of the other fusion proteins.

In the practice of the invention, the fluorescence of fusion proteins can be monitored by any suitable method. For example, fluorescence of fusion proteins can be detected by a fluorometer, a fluorescence microscope, a fluorescence microplate reader, a fluorometric imaging plate reader, or fluorescence-activated cell sorting.

B. Production of Fusion Proteins

Fusion proteins can be produced in any number of ways, all of which are well known in the art. In one embodiment, the fusion proteins are generated using recombinant techniques. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) Gene 164:49-53.

Recombinant techniques are readily used to clone sequences encoding polypeptides useful in the claimed fusion proteins that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci. USA* (1982) 79:6409.

Once coding sequences have been isolated and/or synthesized, they can be cloned into any suitable vector or replicon for expression. (See, also, Examples). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV 1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the fusion proteins described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorphs, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the fusion proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon ($\gamma$ or $\alpha$) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., *Protein Purification Applications: A Practical Approach*, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from Galanthus nivalis agglutinin (GNA), Lens culinaris agglutinin (LCA or lentil lectin), Pisum sativum agglutinin (PSA or pea lectin), Narcissus pseudonarcissus agglutinin (NPA) and Allium ursinum agglutinin (AUA). The choice of a suitable affinity resin is within the skill in the art. After affinity purification, the polypeptides can be further purified using conventional techniques well known in the art, such as by any of the techniques described above.

Polypeptides can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis. These methods are typically used for relatively small polypeptides, i.e., up to about 50-100 amino acids in length, but are also applicable to larger polypeptides.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Polypeptide analogs can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

C. Kits

Fusion proteins or nucleic acids encoding them can be provided in kits with suitable instructions and other necessary reagents for preparing or using the fusion proteins, as described above. The kit may contain in separate containers fusion proteins, or recombinant constructs for producing fusion proteins, and/or cells (either already transfected or separate). Additionally, instructions (e.g., written, tape, VCR, CD-ROM, DVD, etc.) for using the fusion proteins may be included in the kit. The kit may also contain other packaged reagents and materials (e.g., transfection reagents, buffers, media, and the like).

D. Applications

The fusion proteins of the invention provide useful tools for spatially and temporally controlling protein activity with light and will find numerous applications in basic research and development. In particular, fusion proteins can be designed to block or induce activities of proteins of interest, control their interactions with other macromolecules, or direct their subcellular localization. Because fusion proteins can potentially be used to control diverse cellular processes with light, they will be especially useful in the study of protein function in physiological processes and disease mechanisms.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Optical Control of Protein Activity by Fusion to Fluorescent Protein Domains

Introduction

Here, we describe the discovery of an engineered protein interaction that is controlled by cyan light and requires no cofactors. We use this light-controlled association to develop a simple generalizable design for light-inducible proteins. We created a fluorescent light-inducible protein design in which Dronpa domains are fused to both termini of an enzyme domain. In the dark, the Dronpa domains associate and cage the protein, but light induces Dronpa dissociation and activates the protein. This method enabled optical control over guanine nucleotide exchange factor (GEF) and protease domains without extensive screening. Our findings extend the applications of fluorescent proteins from exclusively sensing functions to also encompass optogenetic control.

Dronpa is a monomeric fluorescent protein (FP) derived from the tetrameric parent protein, 22G, isolated from a *Pectiniidae* genus coral (Ando et al. (2004) Science 306:1370-1373). Fluorescence of Dronpa switches off under cyan light (~500 nm) and switches on under violet light (~400 nm) (Ando et al., supra). With off-photoswitching, β strand 7 near the chromophore becomes flexible (Mizuno et al. (2008) Proc. Natl. Acad. Sci. U.S.A. 105:9227-9232); this strand forms part of the cross-dimer interface in the tetrameric parent (Mizuno et al. (2008), supra). A Dronpa mutant with Lys$^{145}$ on β strand 7 changed to Asn (Dronpa145N) is tetrameric at low micromolar concentrations, but dilution promotes monomerization and facilitates off-photoswitching (Mizuno et al. (2010) Photochem. Photobiol. Sci. 9: 239-248). This suggests that multimerization inhibits conformation changes associated with off-photoswitching. We hypothesized, conversely, that conformation changes occurring during off-photoswitching might promote monomerization, whereas on-photoswitching might promote multimerization (FIG. 1A).

Materials and Methods

DNA Construction pcDNA3-mNeptune1-fascin was a gift of Michael W. Davidson (Florida State University, Tallahassee). tdTomato and mCherry plasmids were gifts of Nathan Shaner and Roger Y. Tsien (UCSD). Dronpa145K and Dronpa145N were synthesized by polymerase chain reaction (PCR) of overlapping oligonucleotides and cloned into pNCS, a constitutive bacterial expression vector with a six-consecutive-histidine tag at its N-terminus for purification and BamHI and EcoRI sites for insert cloning (Müller et al. (2008) ChemBioChem 9:2029-2038; herein incorporated by reference). A construct encoding amino acids 1234-1428 of the human intersectin DH domain (Entrez Gene ID 6453) was synthesized by PCR from overlapping oligonucleotides and cloned into the mammalian expression vector pcDNA3 (Invitrogen). Plasmids containing HCV protease and substrate sequences and mRuby2 were previously described (Faix et al. (2009) Int. J. Biochem. Cell Biol. 41:1656-1664; Lam et al. (2012) Nat. Methods 9:1005-1012; herein incorporated by reference).

In addition to pNCS-Dronpa145K and pNCS-Dronpa145N described above, to create other bacterial expression constructs for native polyacrylamide gel electrophoresis, mRuby2, tdTomato, and DsRed2 open reading frames (ORFs) were amplified from pBAD-tdTomato, pcDNA3-mRuby2, and pDsRed2-N1 (Clontech), respectively, and cloned into pNCS. pNCS-tdDronpa145K-Dronpa145N was created by recombination of a PCR-amplified Dronpa145K ORF with BamHI-digested pNCS-Dronpa145N using the In-Fusion recombinase (Clontech).

To create mammalian expression plasmids for fusions of Dronpa and intersectin domains, PCR fragments encoding Dronpa and intersectin DH domains and the Kras4B CAAX sequence (KMSKDGKKKKKKSKTKCVIM, SEQ ID NO:21) were amplified from the above plasmids or from overlapping oligos (for the CAAX sequence), then assembled in a second PCR reaction and cloned into pcDNA3. To create plasmids coexpressing mCherry-substrate-CAAX and fusions of Dronpa and HCV NS4A/NS3 protease, the lentiviral vector pLL3.7 (Addgene) was first modified to reduce its size by replacing the untranslated sequence between PvuII and BspEI sites upstream of the 3' long terminal repeat with a more compact sequence containing only the polypyrimidine tract and integrase att site necessary for reverse transcription and integration, creating pLL3.7m. Then a fusion of mCherry, the NS4A/NS4B substrate sequence, and CAAX was assembled by overlapping PCR and inserted between NheI and EcoRV sites downstream of the CMV promoter by ligation, creating pLL3.7m-mCherry-substrate-CAAX. Finally, PCR fragments encoding a minimal CMV promoter, Dronpa and HCV NS4A/NS3 protease domains, and SV40 polyadenylation signals from pcDNA3 were assembled and inserted between the NotI and XbaI sites of pLL3.7m-mCherry-substrate-CAAX by the In-Fusion recombinase. This created an expression cassette adjacent to and in the opposite transcriptional direction from the original CMV promoter.

In Vitro Protein Characterization and Photoswitching

Bacterial expression plasmids for Dronpa145K, Dronpa145N, tdDronpa145K-Dronpa145N, mRuby, tdTomato, and dsRed2 were transformed into chemically competent *Escherichia coli* strain DH5α for expression. A single colony was inoculated into 100 ml of Luria-Bertani (LB) broth containing 50 μg ml$^{-1}$ ampcillin and incubated overnight at 37° C. The cultures were further incubated at room temperature for another 24 hours, then fluorescent protein purification from bacterial lysates was performed by polyhistidine affinity purification as previously described (Müller et al., supra). Protein concentrations were estimated by absorbance spectrophotometry and purity was verified by SDS-PAGE. For characterization of baseline oligomerization state, 5 μL each of 100 μM, 20 μM, or 10 μM of Dronpa145K or Dronpa145N were run on a 4-16% Bis-Tris native PAGE gel (Invitrogen) with dark cathode buffer alongside 5 μL each of 20 μM mRuby2, tdTomato, and dsRed2 as size controls.

For in vitro photoswitching, purified Dronpa145N and tandem dimer Dronpa145K-Dronpa145N proteins were diluted to 100 μM. Proteins in a 0.2-mL PCR tube were switched off by placement between two cyan LEDs mounted 1 inch apart for 30 minutes (505/30 nm, 170 mW, Thorlab). The fluorescence recovery was conducted by illumination with two similarly mounted UV LEDs for 30 seconds (405/20 nm, 470 mW, Thorlab), followed by incubation at room temperature for 30 minutes. The switching efficiency was estimated by measuring the fluorescence of 1-4 protein aliquots using a Safire 2 monochromator-based fluorescence spectrophotometer (TECAN). In parallel, 2.5 μL (Dronpa145N) or 5 μL (tdDronpa145K-Dronpa145N) of the protein in each condition were loaded on a 4-16% Bis-Tris native PAGE gel (Invitrogen) with dark cathode buffer. 5 μL each of 20 μM mRuby, tdTomato, and dsRed2 were loaded as size controls.

Cell Culture and Transfection

Cells were maintained in high glucose Dulbecco's Modified Eagle Medium (DMEM, HyClone) supplemented with 10% fetal bovine serum (FBS, Invitrogen) and 2 mM glutamine (Sigma) at 37° C. in air with 5% carbon dioxide. Hela cells were transfected at 75-90% confluency with Lipofectamine 2000 (Invitrogen) in 33-mm coverglass-bottom dishes (In Vitro Scientific). Transfections were carried out according to manufacturer's instructions, except that amounts of DNA and transfection reagent were halved to reduce cell toxicity. NIH 3T3 cells (5-7×10$^4$) were plated directly in a transfection solution containing DNA plasmids and Lipofectamine 2000 in 33-mm coverglass-bottom dishes. Amounts of DNA and transfection reagent were reduced to ⅕ of the manufacture-recommended amount for a 33 mm culture. For both HeLa and NIH 3T3 cells, the medium was refreshed 4-6 hours after transfection. HEK293 cells were grown in 8 well-chambered coverglass (Nunc) and transfected at 75-90% confluency using Lipofectamine LTX (Invitrogen) according to the manufacturer's instructions.

Membrane Translocation and Protein Uncaging

In the translocation assay, Hela cells were imaged in PBS at room temperature 12-36 hours after transfection. Imaging was performed with a C-Apochromat 40×1.2 numerical aperture (NA) water-immersion objective on a Zeiss Axiovert 200 M with a Ludl excitation filter controlled by a Ludl MAC 5000 controller, using a Hamamatsu Orca ER Firewire camera. All instruments were controlled by a 2.5 Ghz MacBook Pro computer running Micro-manager 1.4 software in Mac OS 10.6.8. Illumination was provided by a 120-W metal-halide light source (Exfo) passed through a 1-m liquid light guide with a 3 mm core. Dronpa was imaged with a 10% neutral density filter, a 485/30-nm excitation filter, a 505-nm dichroic mirror, and a 525/40 nm emission filter. Neptune was imaged with a 10% neutral density filter, a 560/40 nm excitation filter, a 585 nm dichroic mirror, and a 630/75 emission filter. Dronpa was photoswitched off by illumination using the Dronpa channel excitation and dichroic filters and no neutral density filter for the indicated times. The light intensity was measured to be 4.7 W cm$^{-2}$. Images were acquired within 2 minutes after photoswitching to report Dronpa photoswitching and mNeptune movements. Light passed through a 10% neutral density filter and a 405/20 nm filter and a 440 nm dichroic mirror was used to recover Dronpa fluorescence. Images were acquired immediately to report Dronpa recovery and 5 minutes later to report the mNeptune movements.

For intersectin experiments, NIH 3T3 cells were incubated in serum-free DMEM media for 5-9 hours beginning 32-48 hours after transfection. Cells were then imaged in HBSS at room temperature as described above. Dronpa was photoswitched as described above. Cells were imaged at intervals 5-10 minutes apart for up to 1 hour.

For protease experiments, HEK293 cells were imaged 16 hours after transfection in HBSS with 2% B27 (Invitrogen), 1 mM sodium pyruvate, and 10 mM HEPES pH 7.2 in a TC CU109 chamber (Chamide) heated to 37° C. Imaging was done with an Olympus 40×1.15 NA water immersion objective on Olympus IX80 with a Ludl excitation filter controlled by a Ludl MAC 5000 controller, using a Hamamatsu Orca ER Firewire camera. All instruments were controlled by a 3 GHz Dell Optiplex 755SFF computer running Micro-manager 1.4 software in Windows 7. Illumination was provided by a 120-W metal-halide light source (Exfo) passed through a 1-m liquid light guide with a 3 mm core. Dronpa was imaged with a 485/22 nm excitation filter, 510 nm dichroic mirror, and 540/40 nm emission filter. The mCherry was imaged with a 545/30 nm excitation filter, 570 nm dichroic mirror, and 605/50 nm emission filter. Dronpa was photoswitched off by 10 seconds of illumination using the Dronpa channel excitation and dichroic filters and no neutral density filter. Images were acquired at 10 minutes, 30 minutes and 60 minutes after photoswitching.

Statistical Analysis

To determine statistical significance of light-dependent filopodia induction, the Pearson chi-squared test was performed on the distributions of the two observation outcomes of filopodia induction or no filopodia induction between two treatment conditions of illumination or no illumination. The null hypothesis was that filopodia induction is independent of treatment condition. A responding cell was defined as a cell with at least one new filopodium per polygonal side.

Results

Figure 1B:
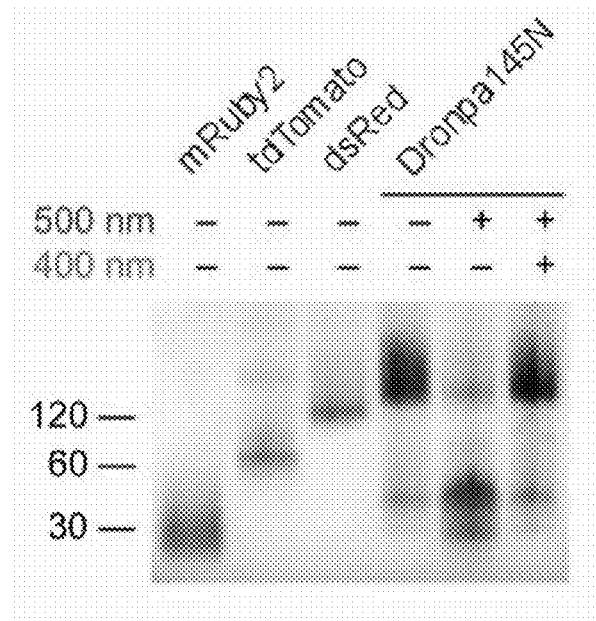
Figure 1C:
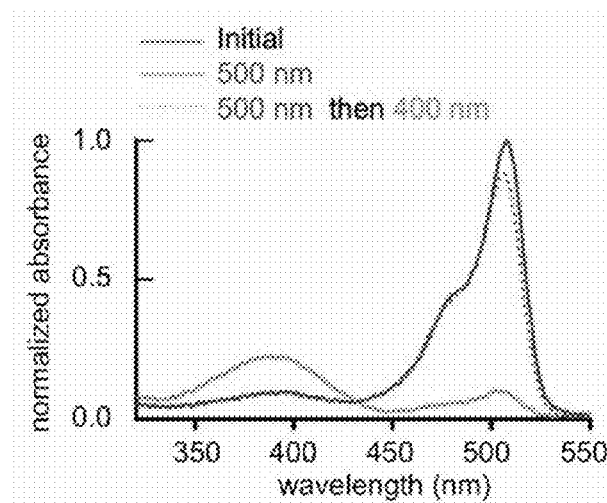
Figure 5A:
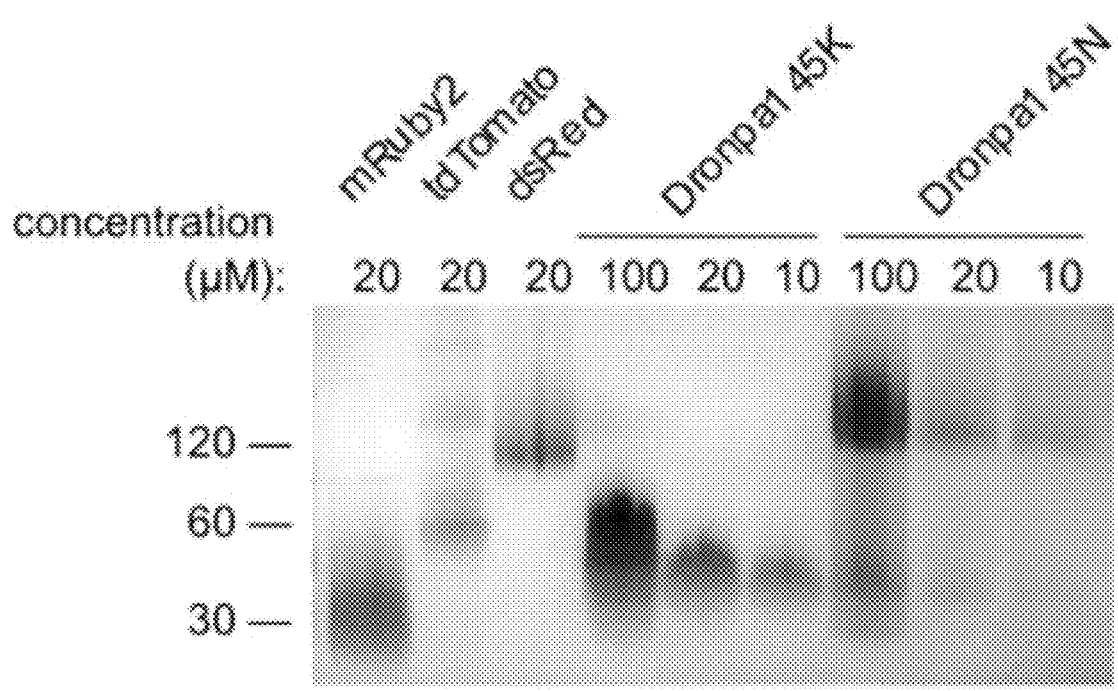
FIGS. 5A-5C show quantification of reversible photoswitching of recombinant Dronpa constructs by fluorescence in vitro.
Figure 5B:
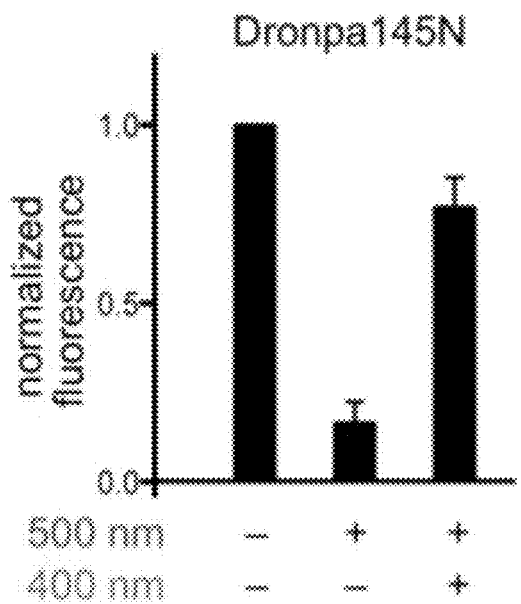

To determine if light could control Dronpa145N multimerization, we performed native polyacrylamide gel electrophoresis (PAGE). Dronpa145N was tetrameric at concentrations from 10 to 100 μM in the initial bright state, whereas wild-type Dronpa (Dronpa145K for clarity; K, Lys) was monomeric (FIG. 5A). Cyan illumination of 100 μM Dronpa145N induced a shift from a cyan-absorbing to a violet-absorbing species (FIG. 1C) and a loss of green fluorescence (FIG. 5B), as previously described (Ando et al. (2004) Science 306: 1370-1373). Simultaneously, Dronpa145N redistributed from tetrameric toward monomeric species (FIG. 1B, lane 2), implying that off-photoswitched Dronpa145N has a dissociation constant exceeding 100 μM. Violet light restored cyan absorbance (FIG. 1C) and green fluorescence (FIG. 5B) and also induced retetramerization (FIG. 1B, lane 3), indicating that monomerization was not due to irreversible protein damage. These results show that Dronpa145N interactions can be controlled by light.

Figure 1D:
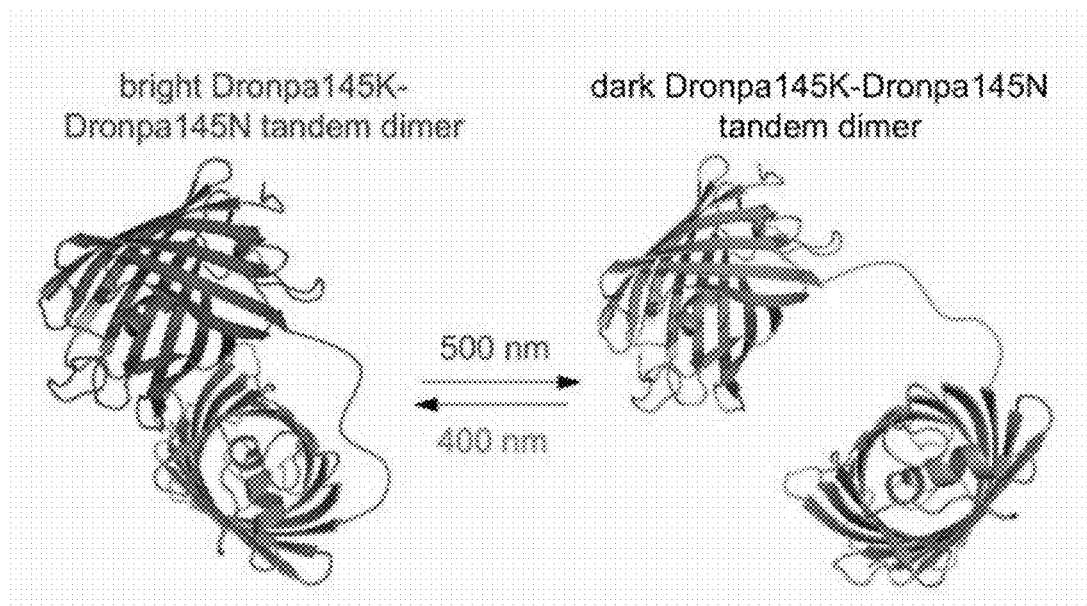
Figure 1E:
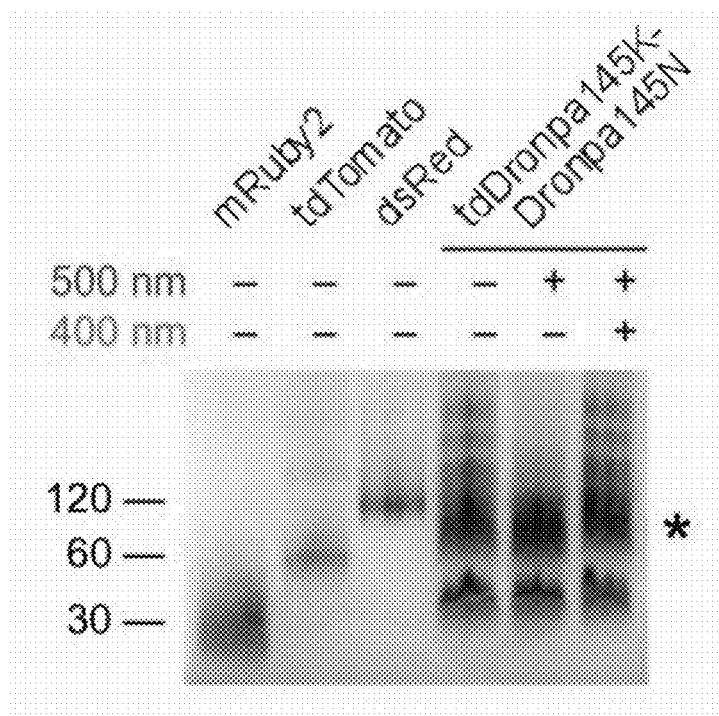
Figure 1F:
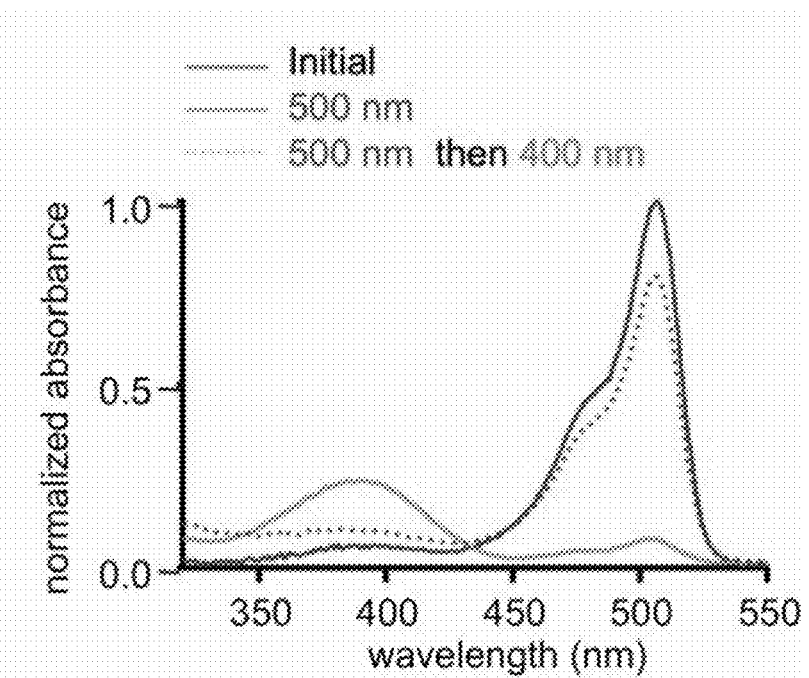
Figure 5C:
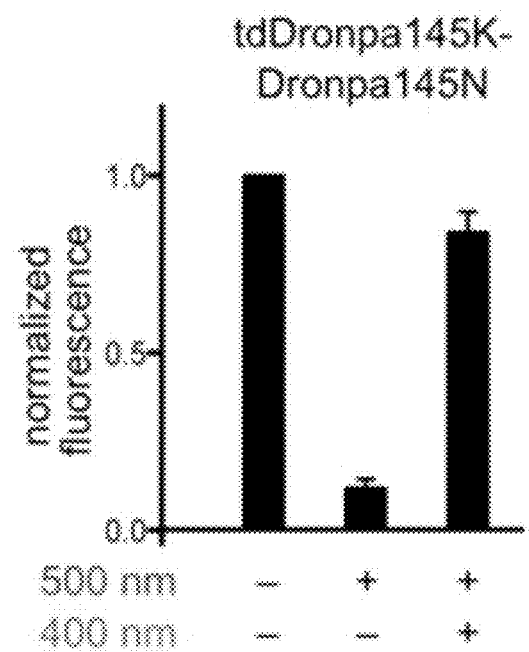

A dimer-to-monomer conversion might be more easily harnessed to control protein activity than a tetramer-to-monomer conversion. Given the lack of multimerization of Dronpa 145K, we explored whether oligomerization of Dronpa145K and Dronpa145N could be limited to dimerization. To achieve high effective concentrations of Dronpa145K and Dronpa145N without driving Dronpa145N tetramerization, we fused Dronpa145K in tandem to Dronpa145N via a linker (K-N tandem dimer) (FIG. 1D). The effective concentration of one domain relative to another on the same polypeptide has been estimated at ~70 μM (Müller et al., supra). The K-N construct migrated in native PAGE primarily as expected for a tandem dimer (FIG. 1E). If the Dronpa domains were engaged in a light-sensitive intramolecular interaction, illumination should induce dissociation, resulting in a more elongated faster-migrating conformation. Indeed, the tandem dimer migrated faster after cyan illumination, and this process was reversed after violet light-induced recovery (FIG. 1E). Expected transitions between cyan- and violet-absorbing forms were again observed (FIG. 1F and FIG. 5C). Thus, the K-N tandem dimer undergoes reversible light-induced conformational changes consistent with dissociation and reassociation of Dronpa domains.

Figure 2A:
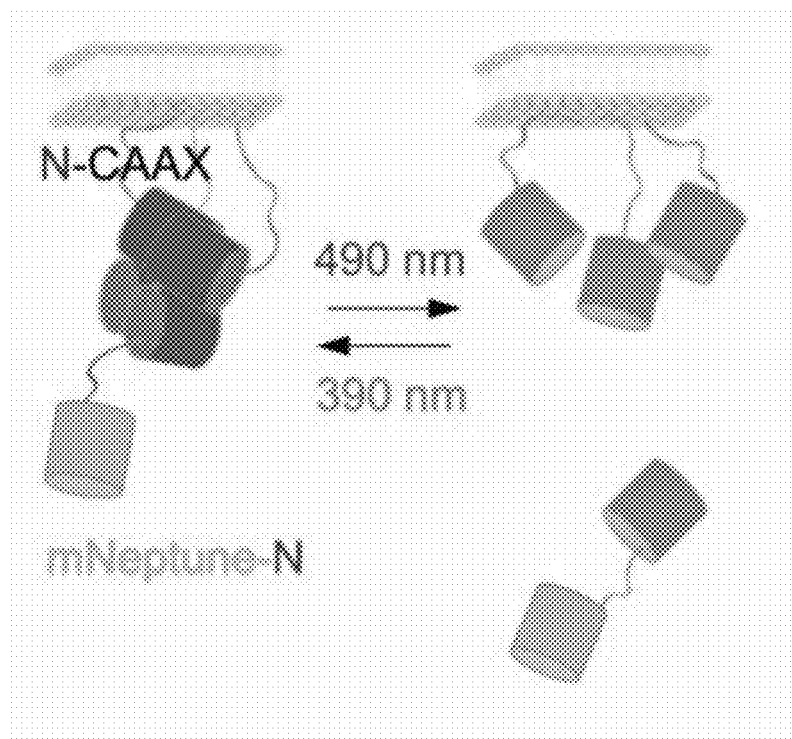
FIGS. 2A-2H show the control of photochromic FP domain association by light in cells.
Figure 2B:
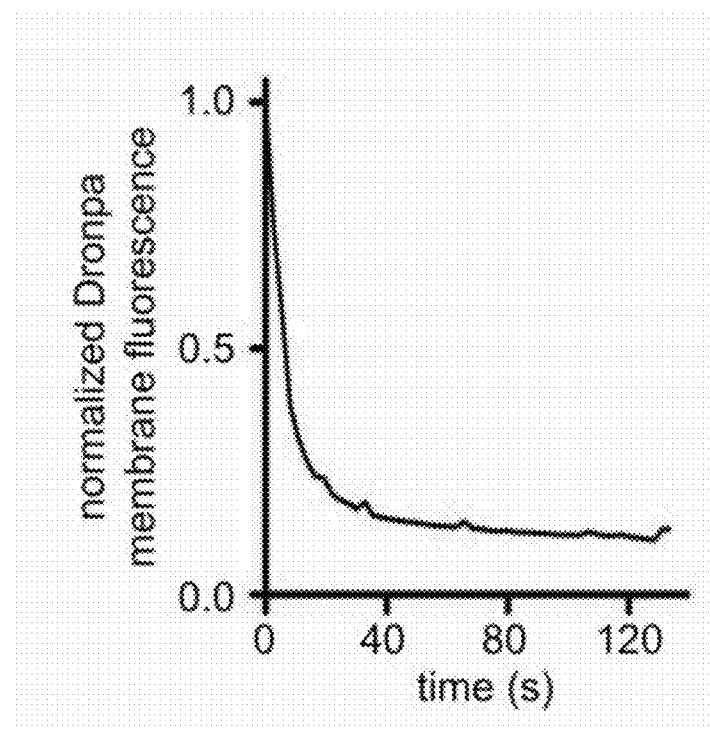
Figure 2C:
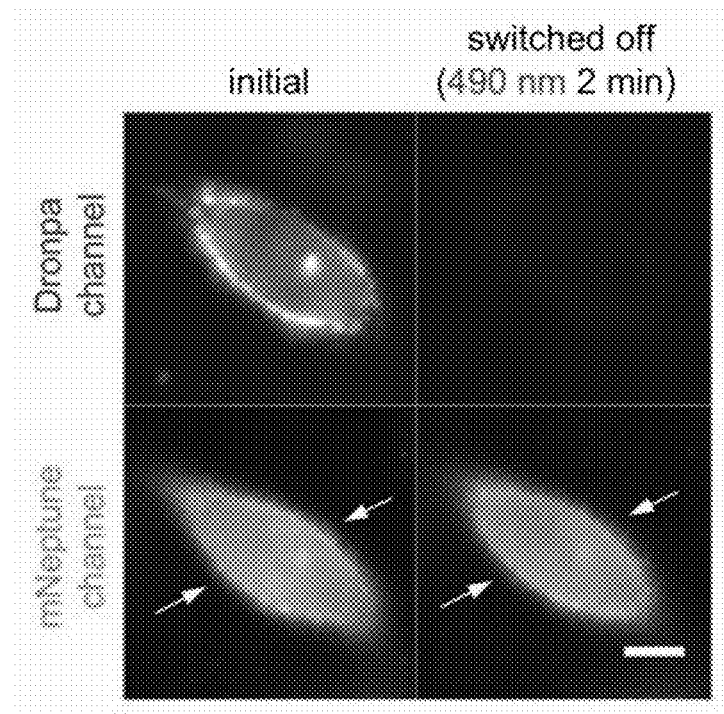
Figure 2D:
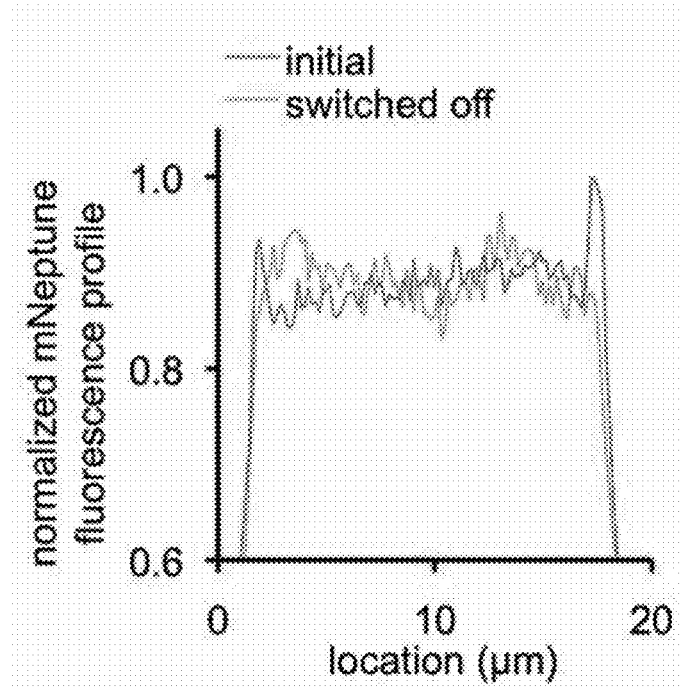

To determine whether light-induced Dronpa145N dissociation could occur in mammalian cells, we created two fusions: N-CAAX, a fusion of Dronpa145N to the membrane-anchoring K-Ras C-terminal farnesylation motif (CAAX box), and mNeptune-N, a fusion of the far-red FP mNeptune to Dronpa145N (FIG. 2A) (Lin et al. (2009) Chem. Biol. 16:1169-1179). Upon 10-fold relative overexpression of N-CAAX to insure an excess of membrane-localized Dronpa, some mNeptune-N was membrane-bound through Dronpa145N oligomerization (FIGS. 2C and 2D). Cyan light switched off Dronpa fluorescence (FIG. 2B) and resulted in the release of mNeptune from the membrane (FIGS. 2C and 2D). Release required prolonged exposures (2 minutes, metal halide lamp at 100% neutral density through a 40×1.2-numerical aperture lens) and was only partial, but nevertheless indicated that light could induce Dronpa domain dissociation in cells.

Figure 2E:
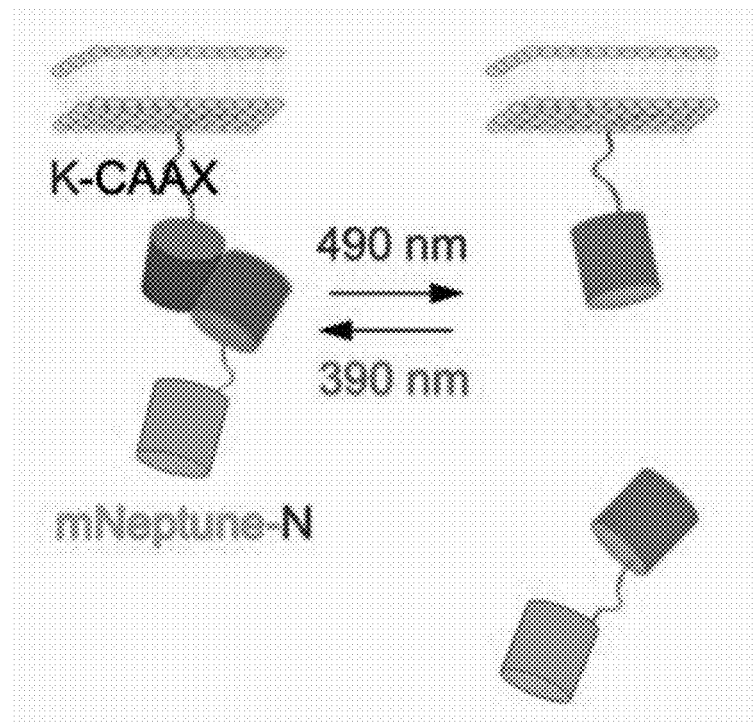
Figure 2F:
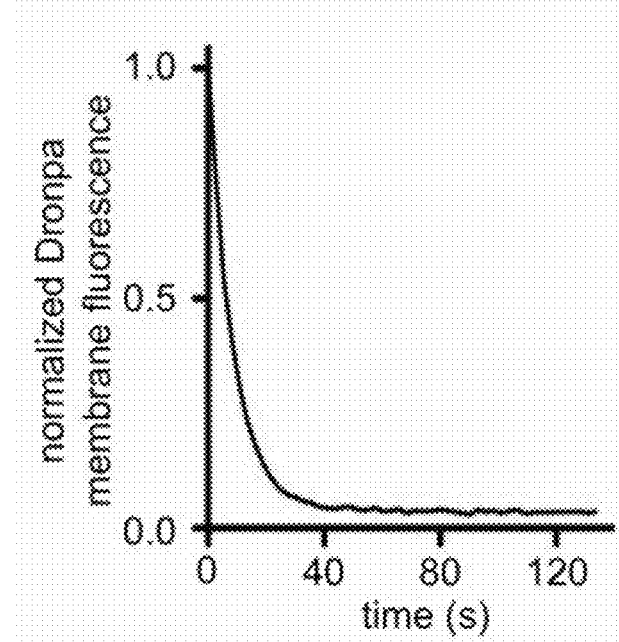
Figure 2G:
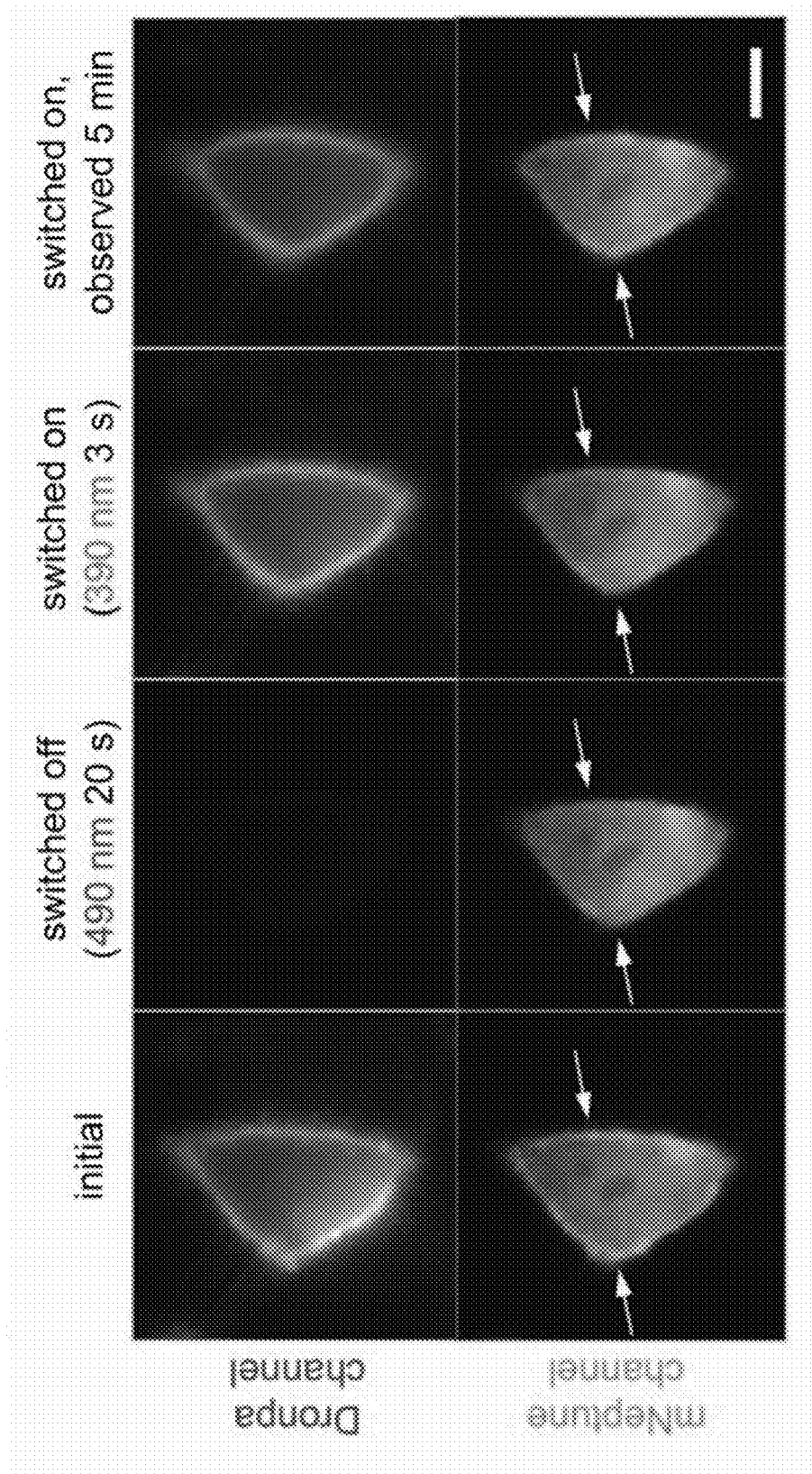
Figure 2H:
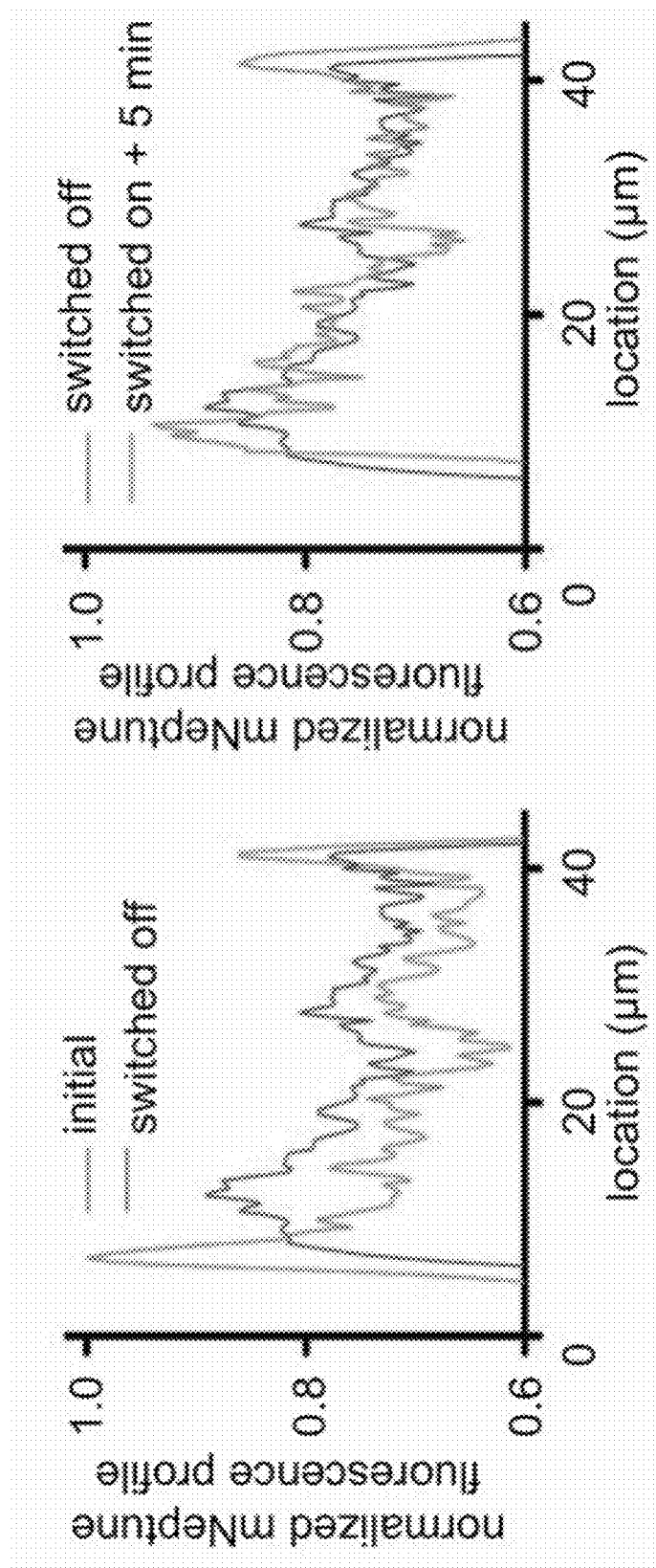
Figure 6A:
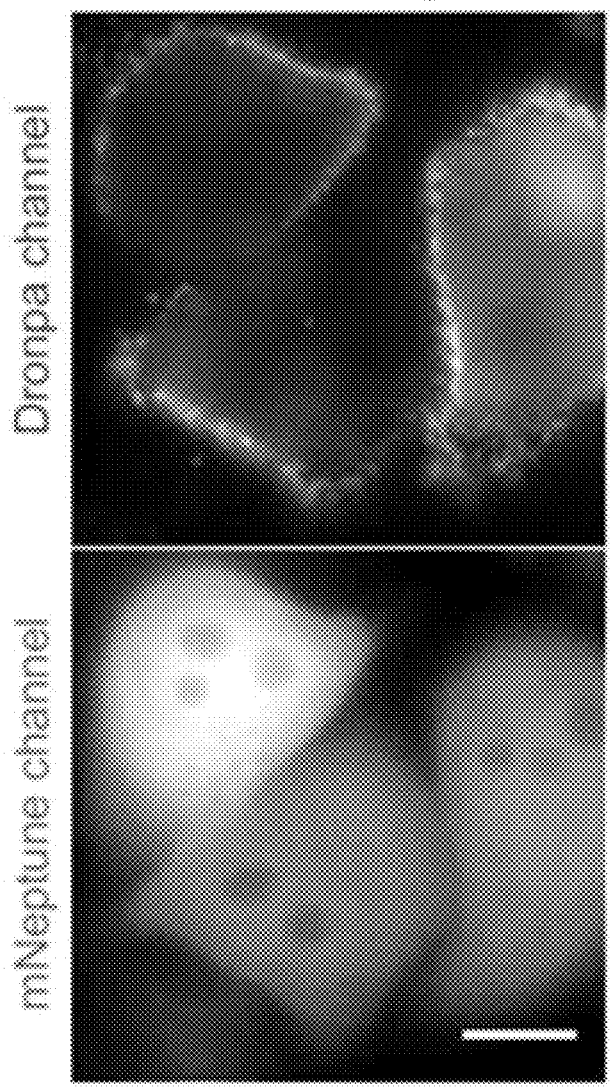
FIGS. 6A and 6B show the directional specificity of membrane recruitment of Dronpa.
Figure 6B:
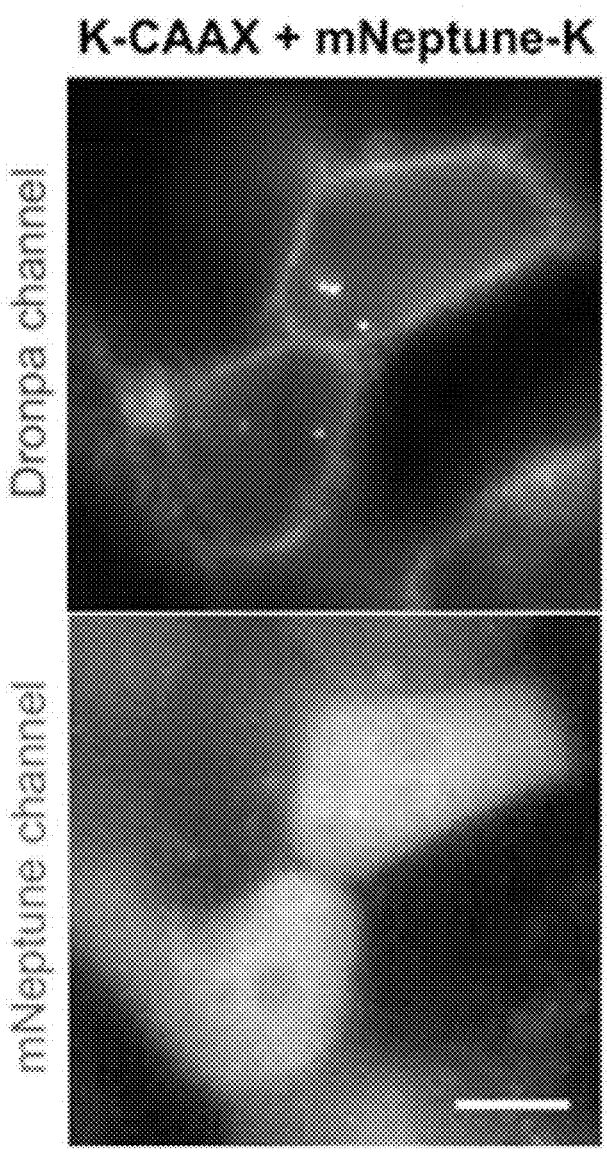

To find conditions for Dronpa domain dissociation that require less light, we explored Dronpa145K-Dronpa145N heterodimerization (FIG. 2E). Dronpa145K-CAAX (K-CAAX) was able to recruit mNeptune-N to the membrane (FIG. 2G). Off-photoswitching of membrane fluorescence was faster than with N-CAAX (FIG. 2F), and release of mNeptune required only 20 seconds of illumination (FIGS. 2G and 2H). On-photoswitching of Dronpa by violet light induced membrane re-localization of mNeptune-N (FIGS. 2G and 2H). Reversing the positions of Dronpa domains by expressing N-CAAX and mNeptune-Dronpa145K (mNeptune-K) did not result in a membrane mNeptune signal (FIG. 6A), perhaps because tetramerization between concentrated N-CAAX molecules outcompeted weaker heterodimerization with mNeptune-K. Use of only monomeric Dronpa domains (K-CAAX and mNeptune-K) also resulted in no membrane mNeptune (FIG. 6B), as expected.

Figure 7A:
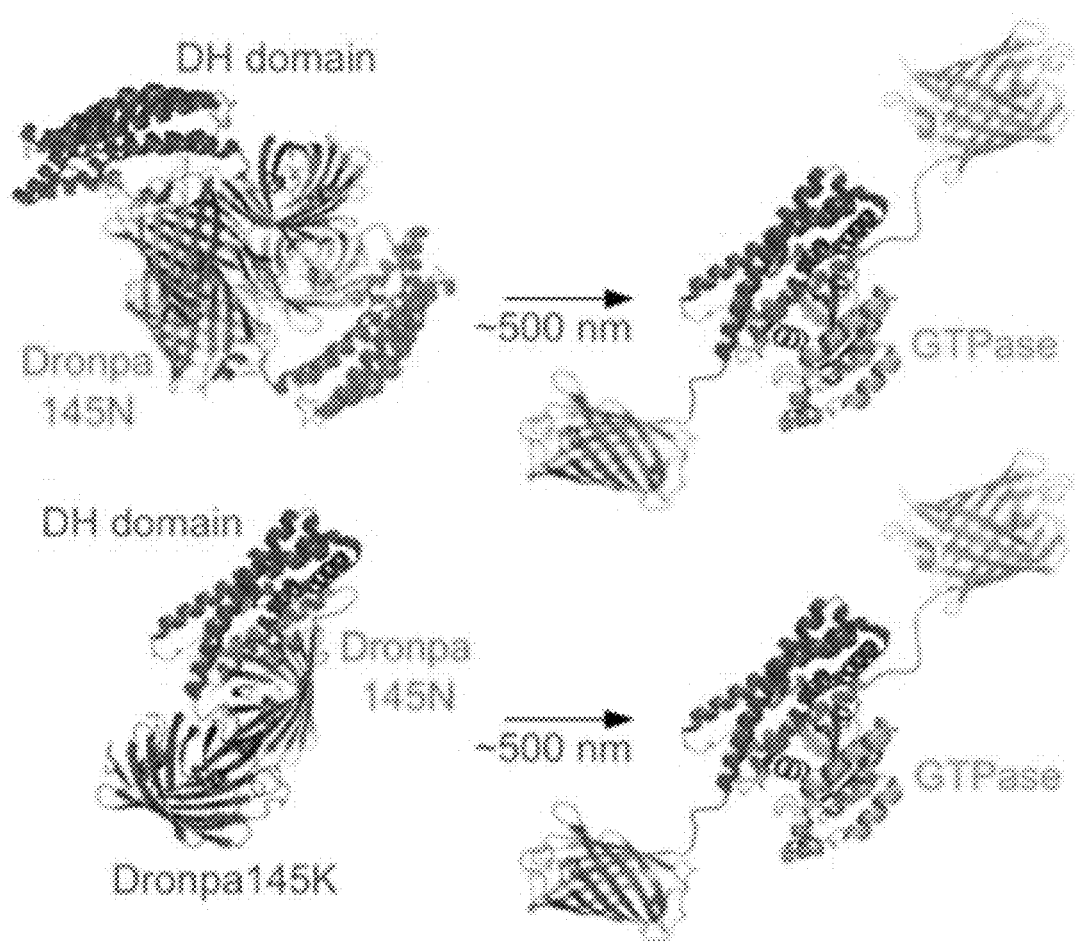

We hypothesized that we could use Dronpa to build light-controllable single chain proteins. Specifically, we hypothesized that protein functions could be blocked by fusing Dronpa domains to the amino terminus (NT) and the carboxyl terminus (CT) (FIG. 7A). Binding of the two Dronpa domains would "cage" the protein in an inactive state by masking surfaces required for binding interaction partners or substrates, similarly to auto-inhibition of many kinases (Leonard et al. (2007) Cell 129:1037-1038), transcription factors (Pufall et al. (2002) Annu Rev. Cell Dev. Biol. 18:421-462), and guanine nucleotide exchange factors (GEFs) for monomeric guanosine triphosphatases (GTPases) (Yu et al. (2010) Cell 140:246-256). Protein function could then be induced by light-mediated dissociation of the Dronpa domains (FIG. 7A).

Figure 7C:
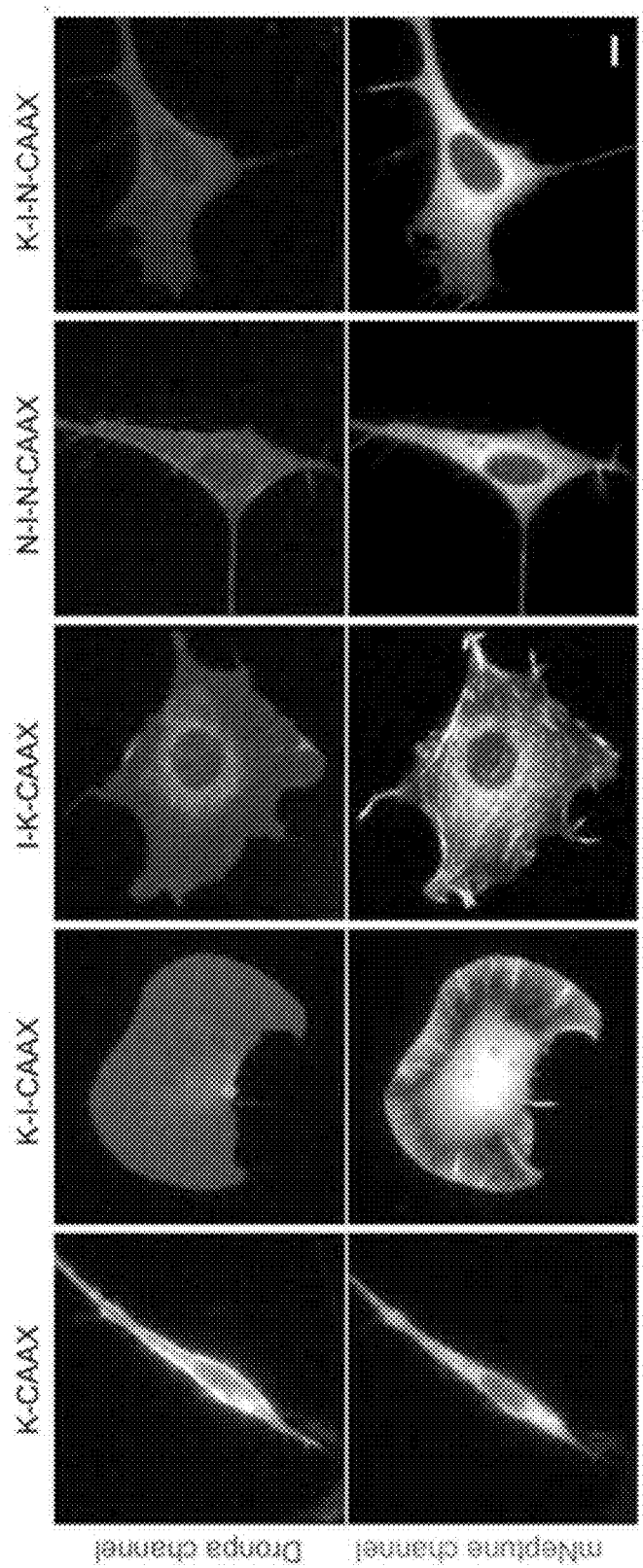
Figure 7D:
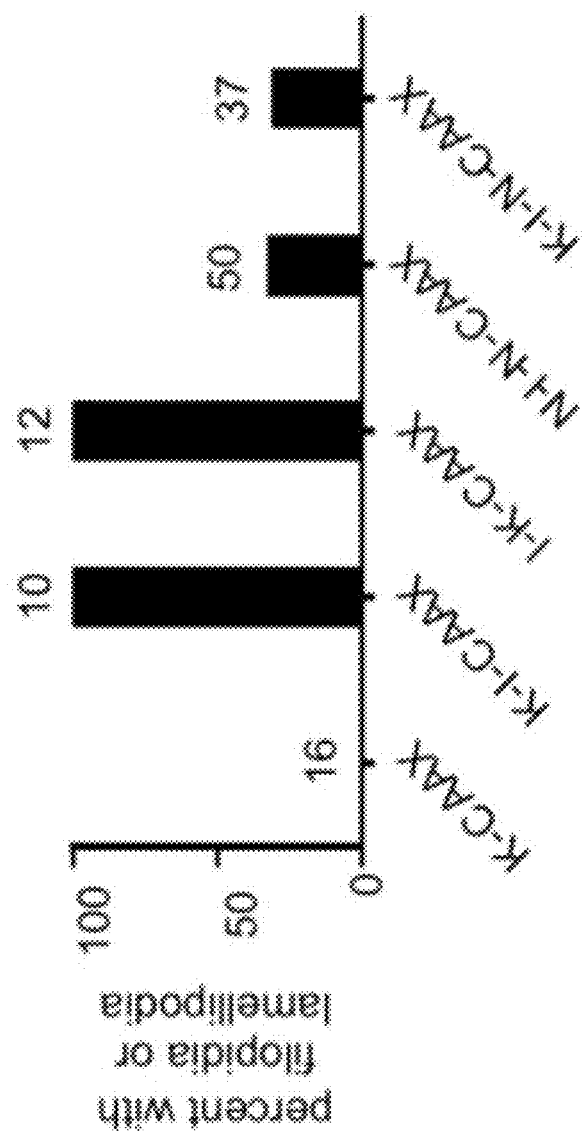
Figures 8A, 8B:
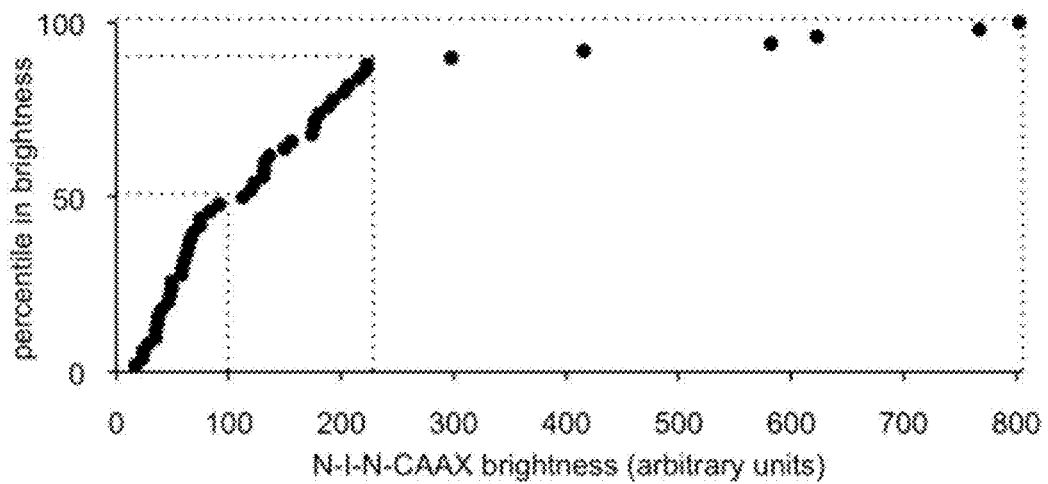
FIGS. 8A-8D show the quantitation of filopodia and lamellipodia production by Dronpa-intersectin fusion constructs at different expression levels.
Figures 8C, 8D:
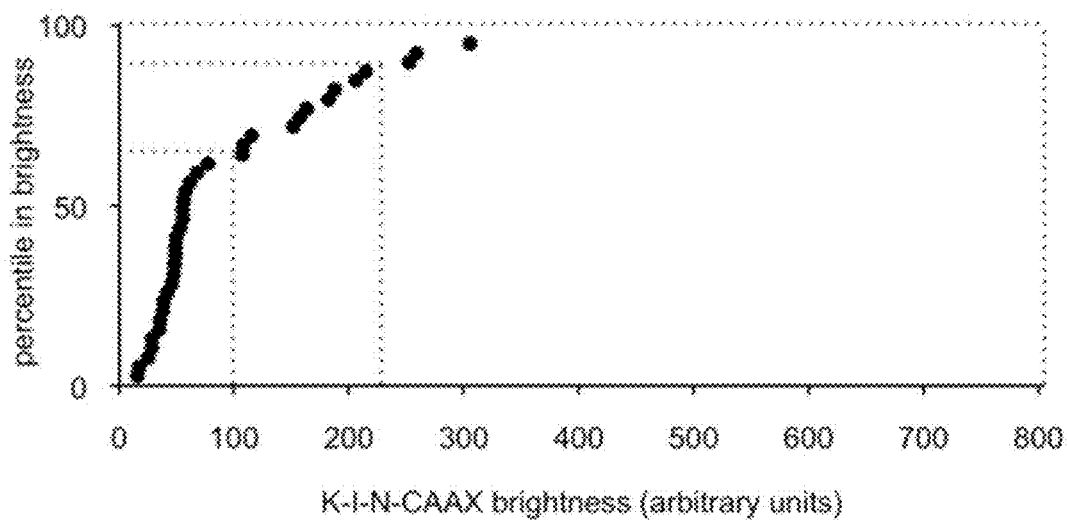

We first controlled the Cdc42 GEF intersectin, which can be inactivated by terminal circularization (Yeh et al. (2007) Nature 447:596-600). We fused Dronpa145K or Dronpa145N at the NT of the intersectin Dbl homology (DH) domain and Dronpa145N at the CT followed by the CAAX sequence, creating K-I-N-CAAX and N-I-N-CAAX (FIG. 7B). As catalytically active controls, we fused Dronpa145K to either side of intersectin (K-I-CAAX and I-K-CAAX) (FIG. 7B). We coexpressed these constructs in fibroblasts with a mNeptune-fascin reporter to mark filopodia and lamellipodia (Adams (2004) Curr. Opin. Cell Biol. 16:590-596). I-K-CAAX or K-I-CAAX robustly induced filopodia and lamellipodia (FIGS. 7C and 7D), as expected for Cdc42 activation, which induces filopodia directly and lamellipodia directly via the formin-family protein FMNL2 and indirectly via Rac (Block et al. (2012) Curr. Biol. 22:1005-1012; Nishimura et al. (2005) Nat. Cell Biol. 7:270-277). Cells expressing N-I-N-CAAX and K-I-N-CAAX produced filopodia or lamellipodia at much lower frequencies than I-K-CAAX or K-I-CAAX (FIGS. 7C and 7D). These experiments were performed by transient transfection, which results in variable expression levels. When designated as low, medium, or high expressers by Dronpa fluorescence (FIGS. 8A and 8C), low expressers, which included the majority of cells, exhibited basal filopodia or lamellipodia infrequently (0% for N-I-N-CAAX and 8% for K-I-N-CAAX) (FIGS. 8B and 8D). Thus, fusion of flanking Dronpa domains cages intersectin activity effectively as long as higher expression levels are avoided, similarly to tophototropin-based photoactivable Rac (PA-Rac; Wu et al. (2011) Methods Enzymol. 497:393-407).

Figure 3A:
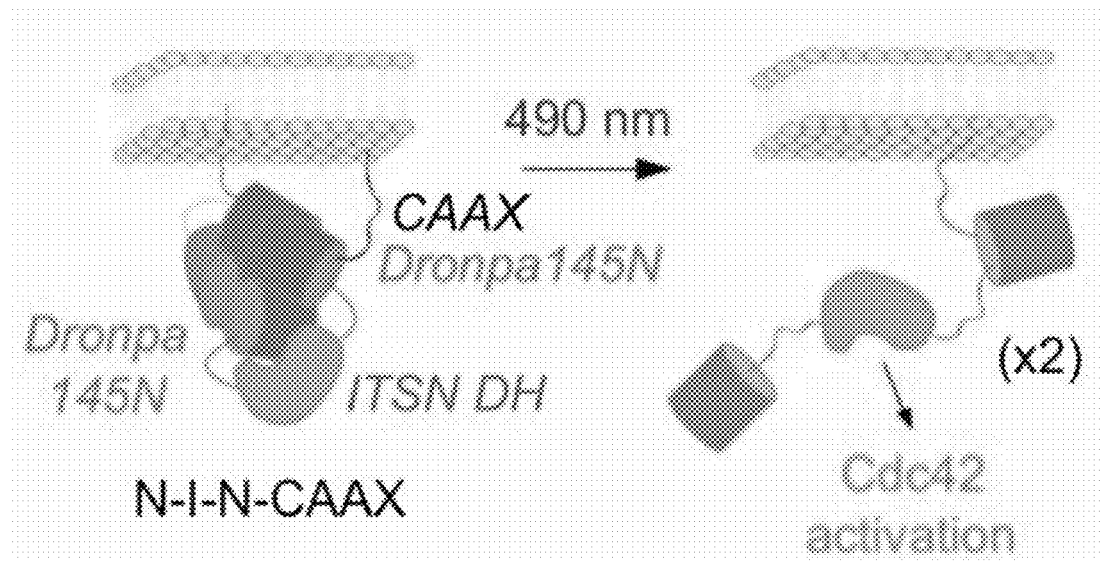
FIGS. 3A-3H show a light-inducible single-chain guanine nucleotide exchange factor (GEF).
Figure 3B:
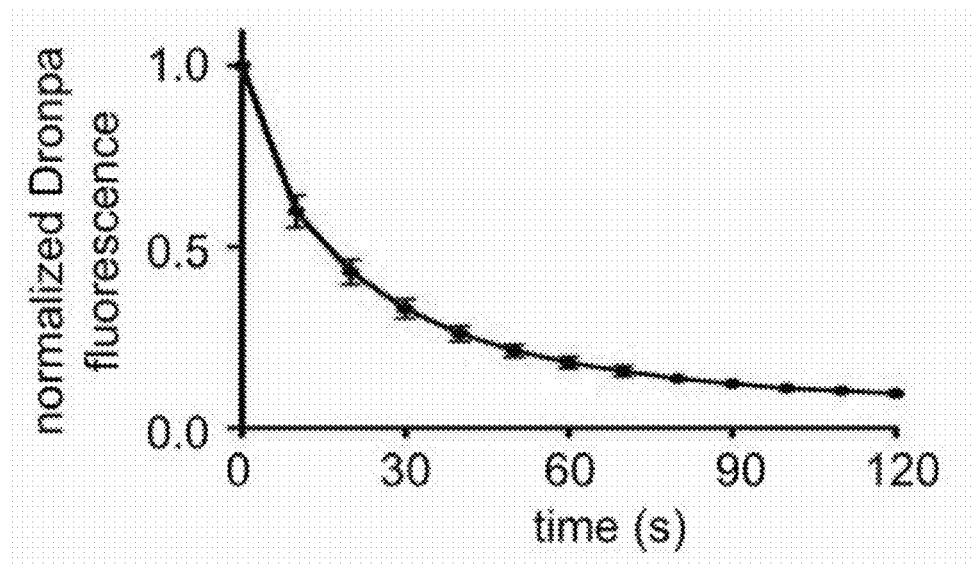
Figure 3C:
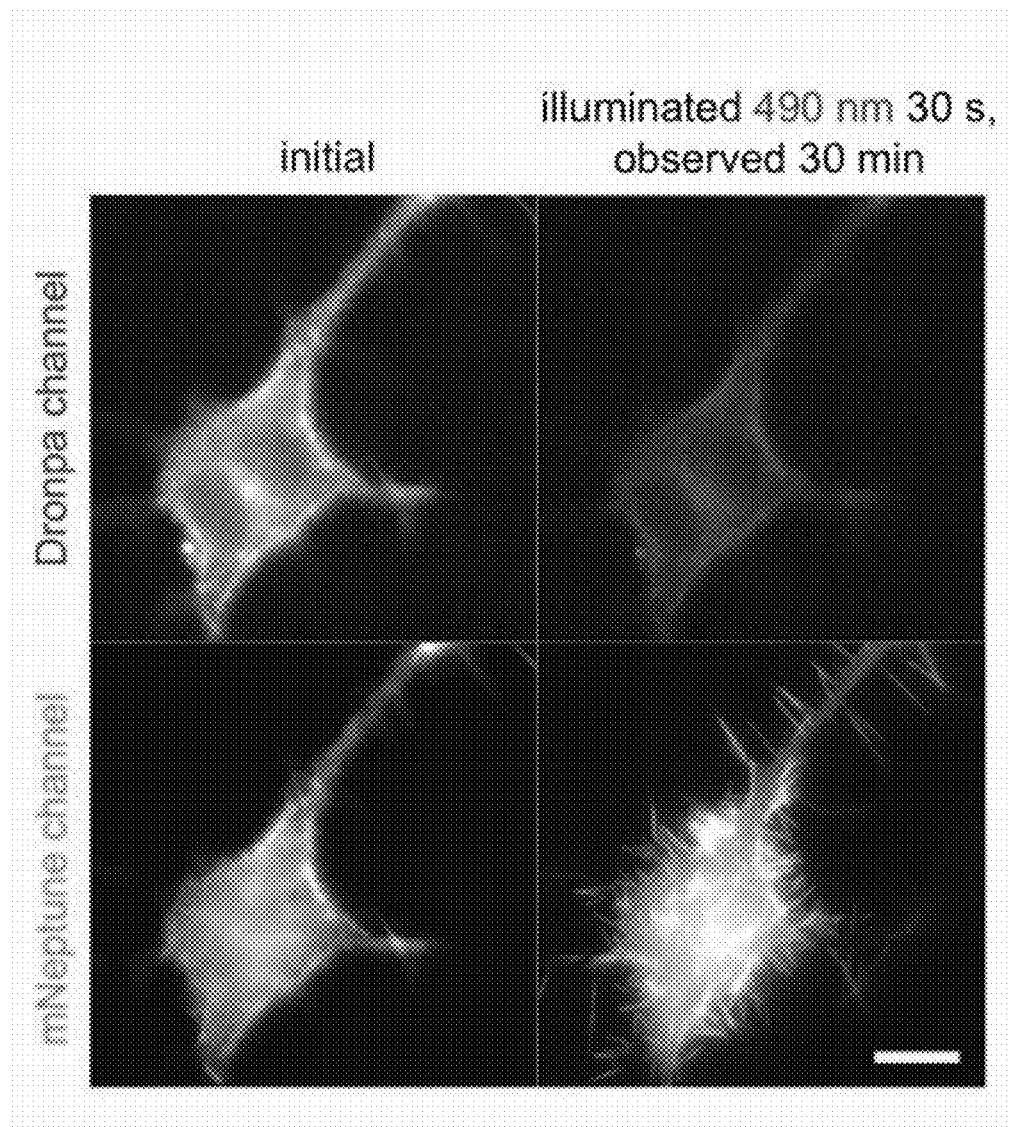
Figure 3D:
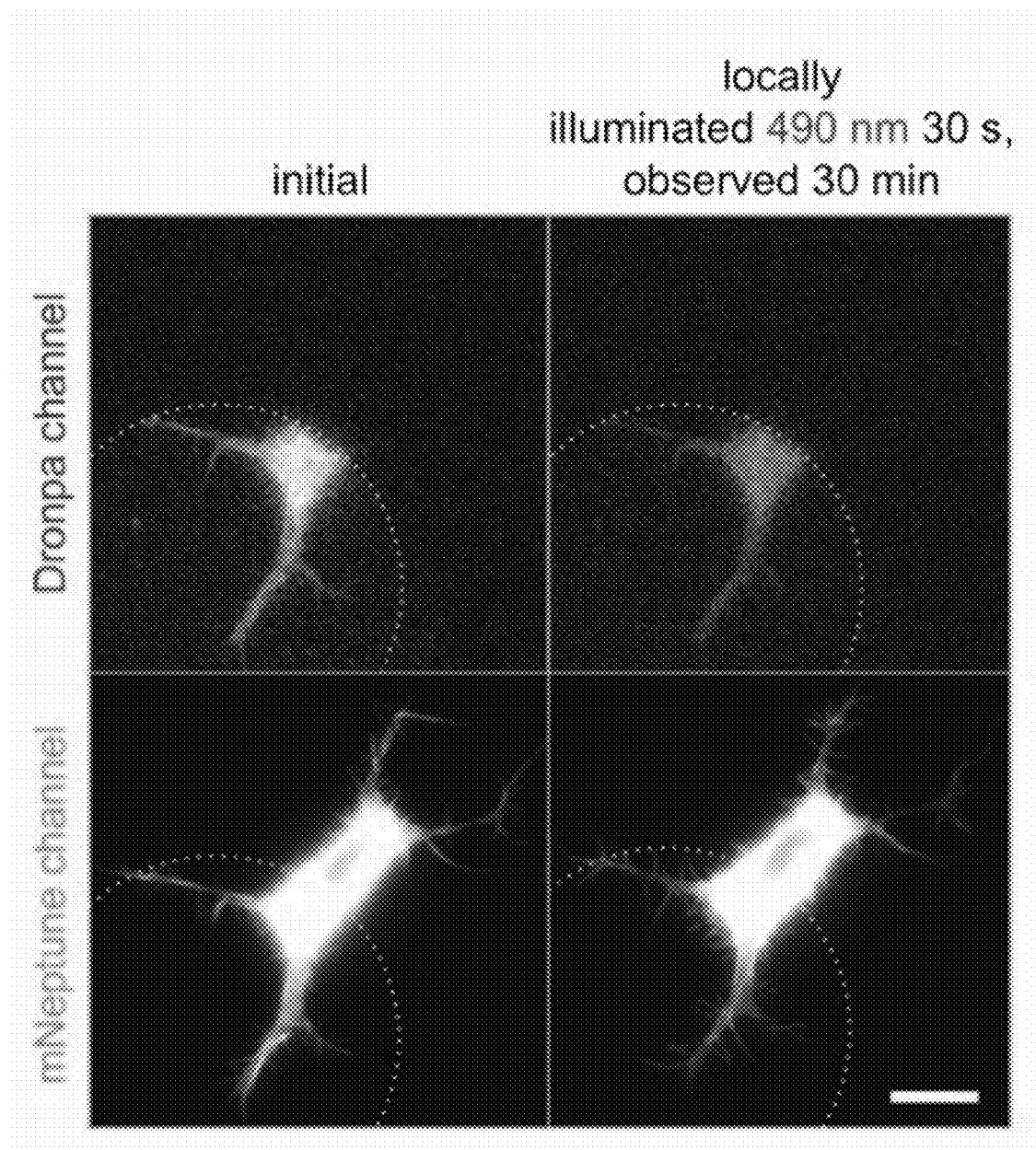
Figure 3E:
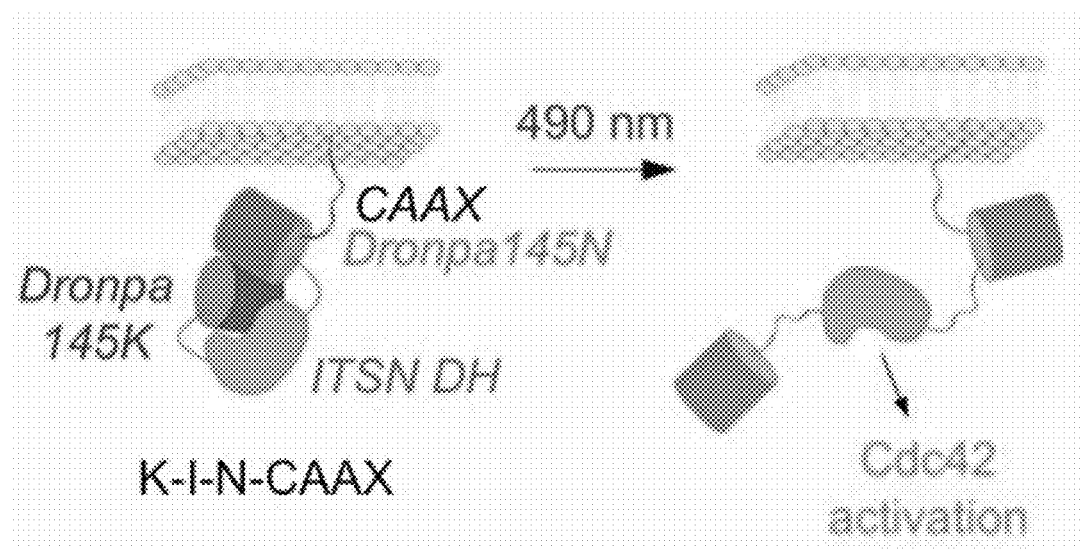
Figure 3F:
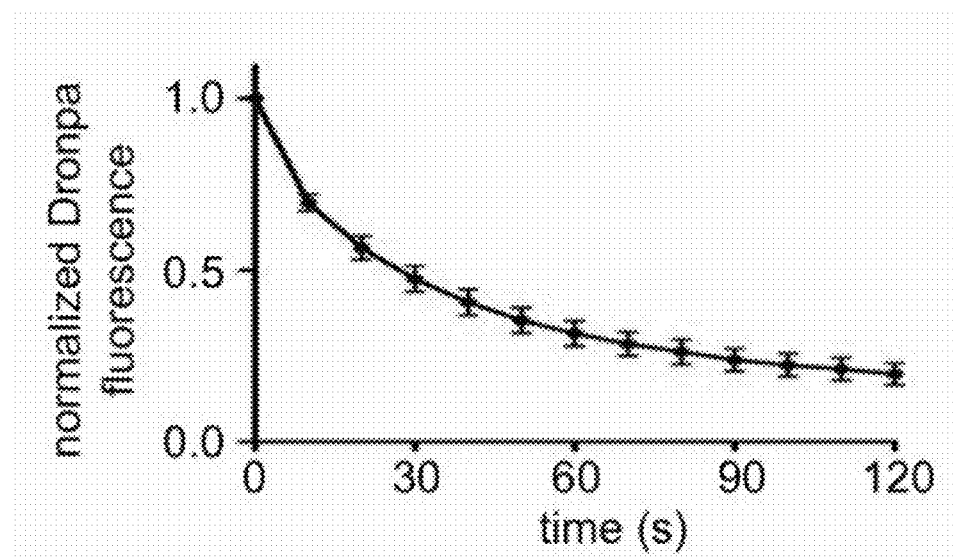
Figure 3G:
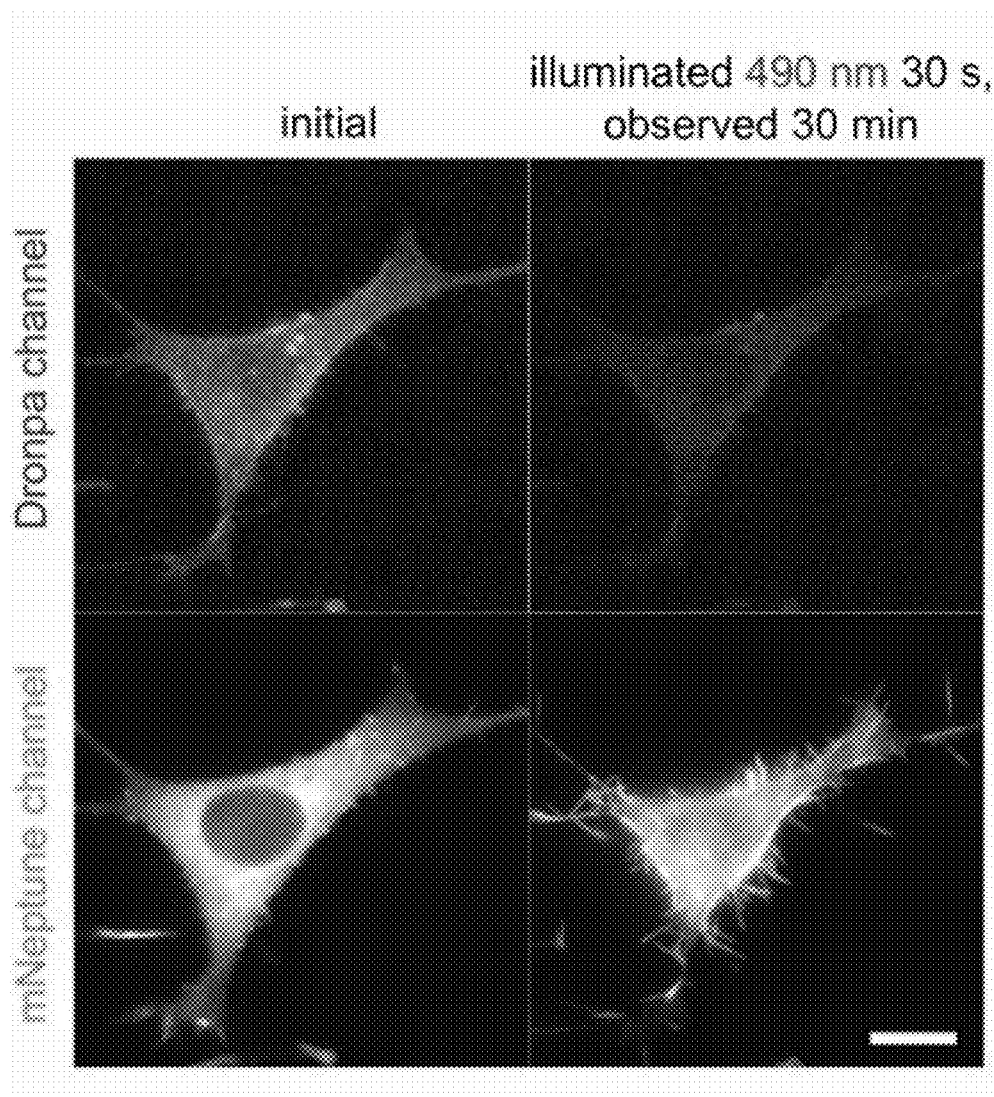
Figure 9A:
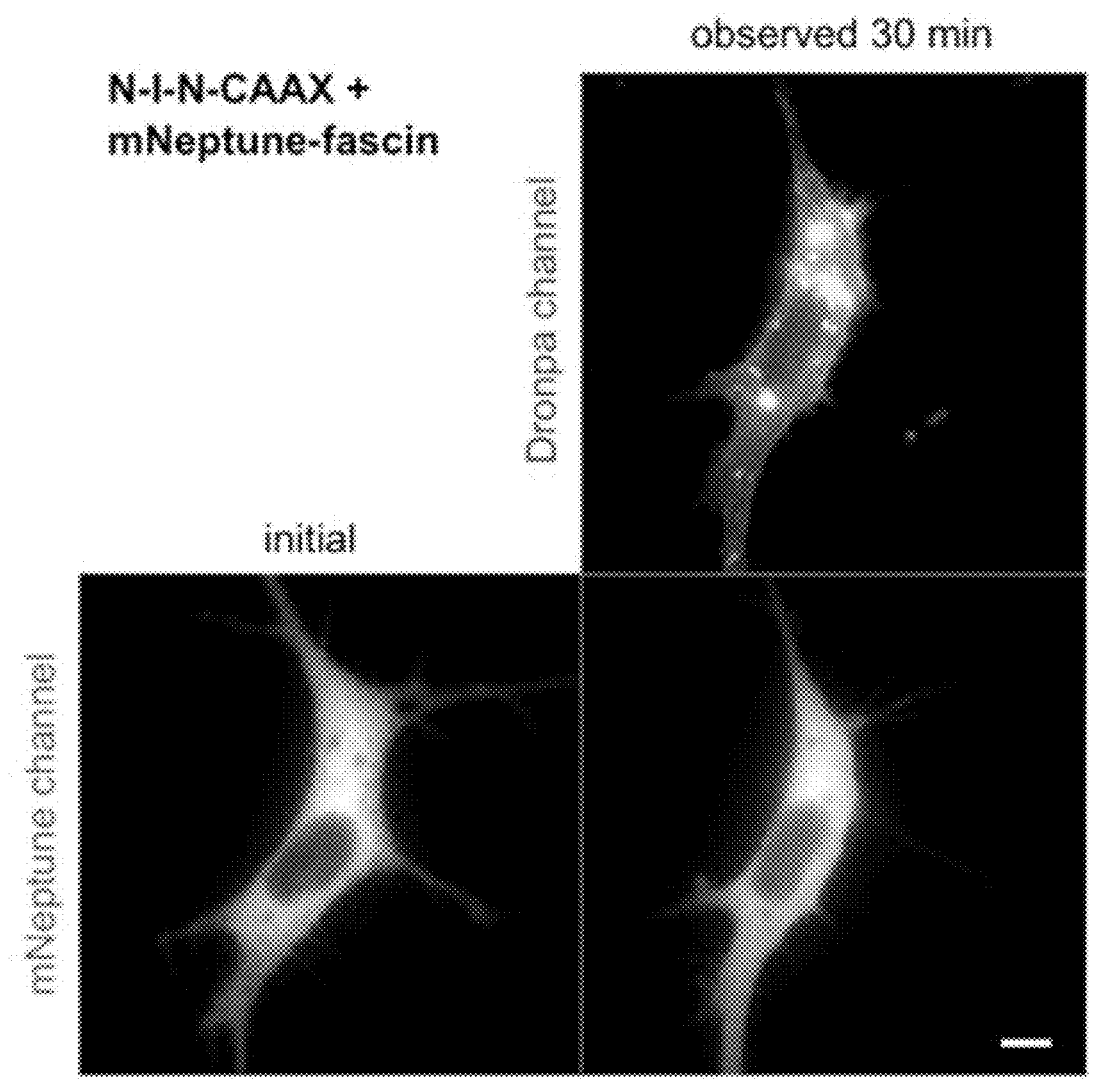
FIGS. 9A-9D show that filopodia induction required both light and a caged ITSN DH protein.
Figure 9B:
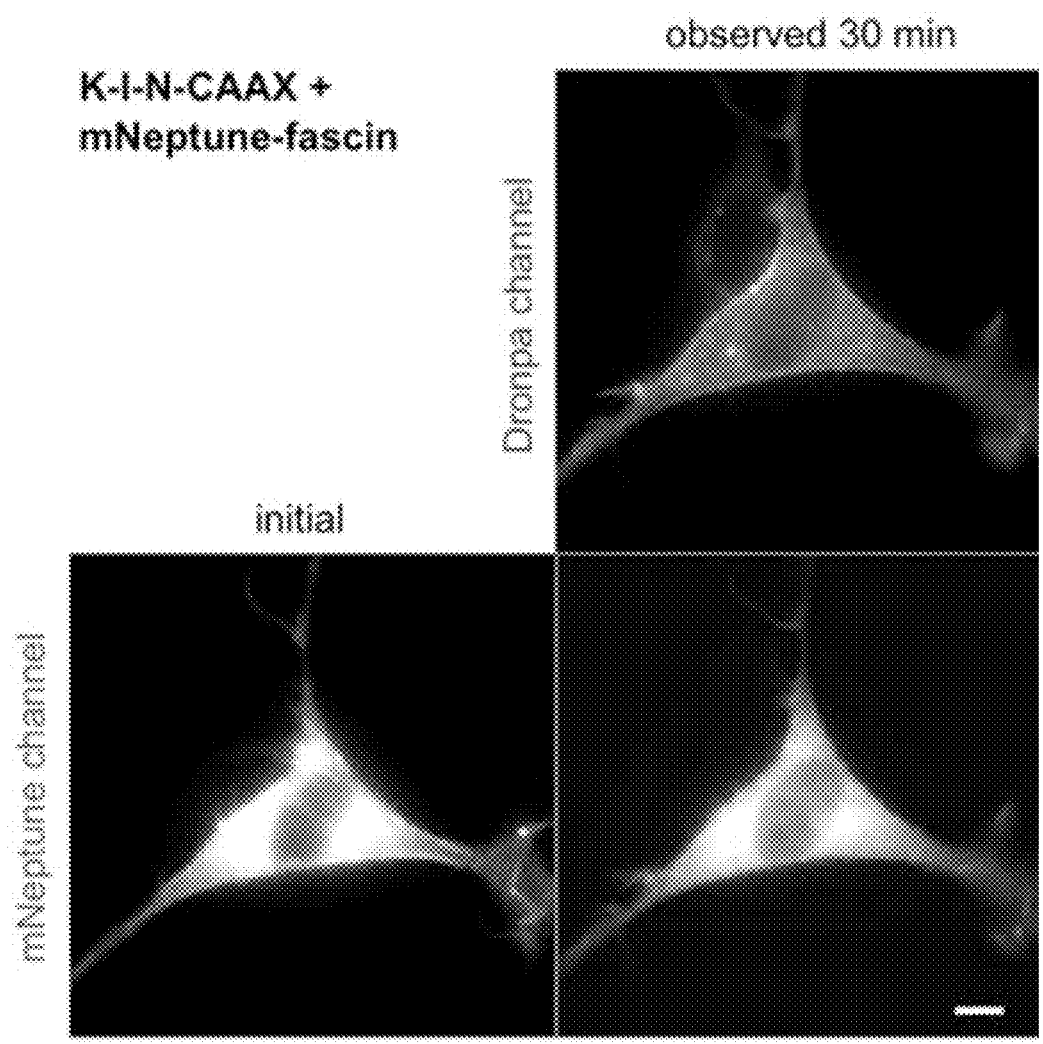
Figure 9C:
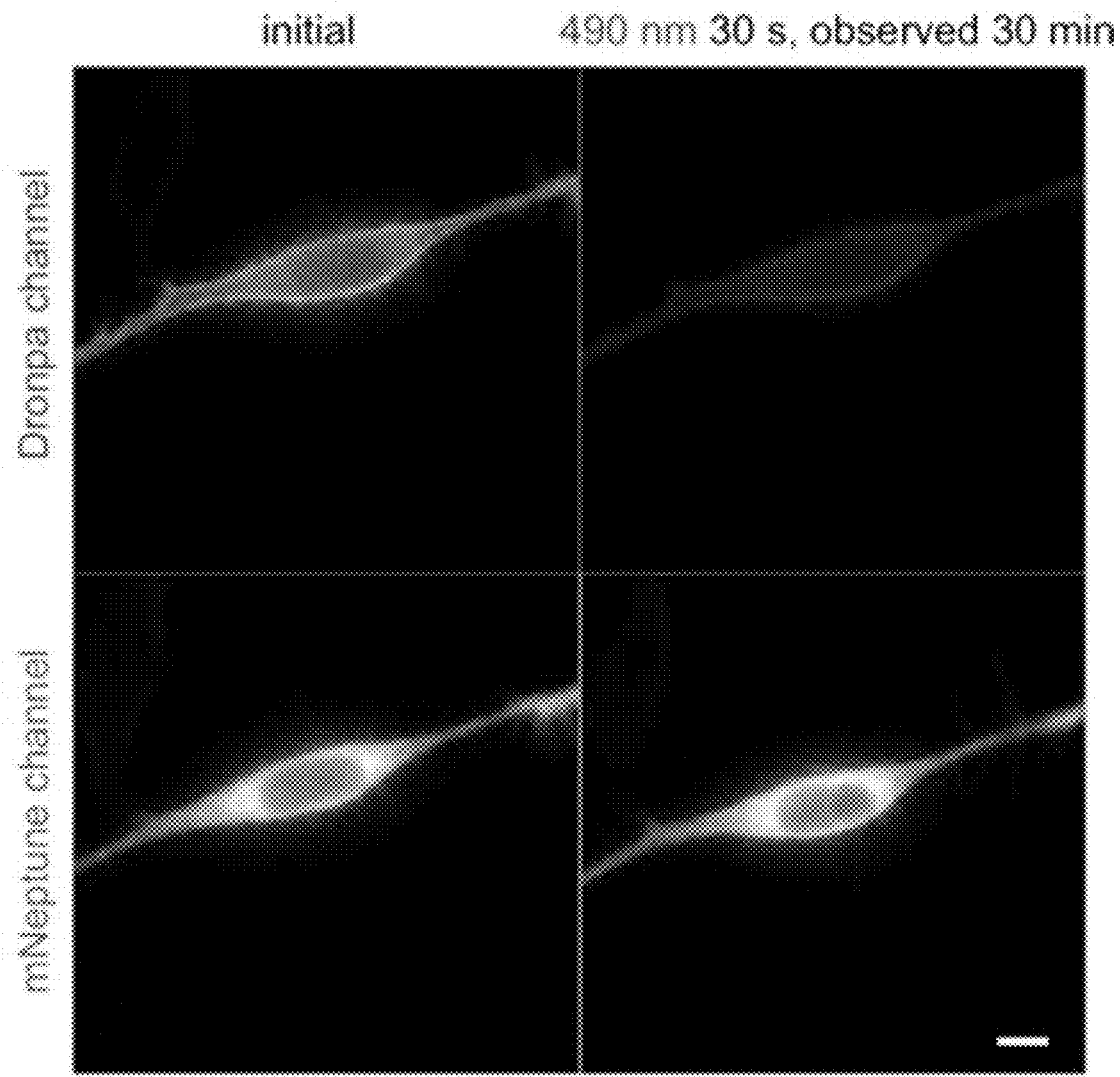
Figure 9D:
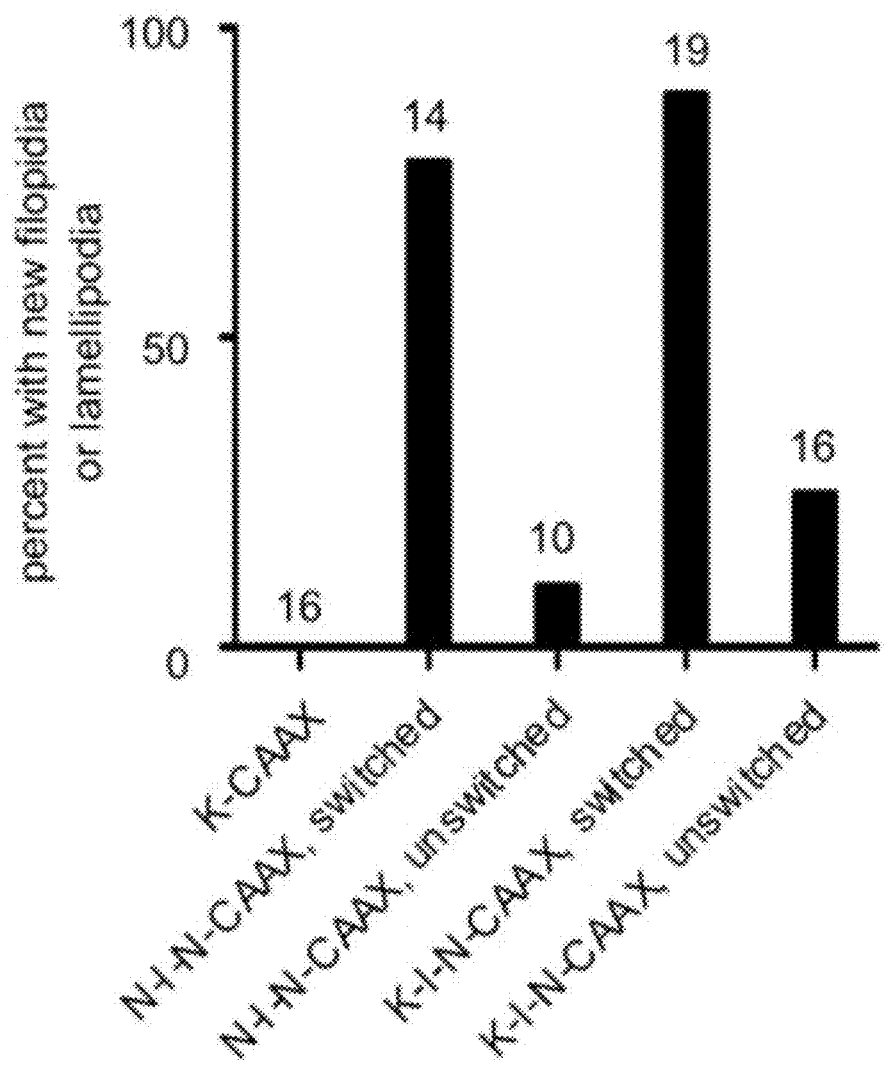

We next asked whether caged intersectins could mediate filopodia or lamellipodia induction by light (FIGS. 3A and 3E). Illumination with 490/20-nm light for 30 seconds switched off more than 50% of the fluorescence in both N-I-N-CAAX- and K-I-N-CAAX-transfected fibroblasts (FIGS. 3B and 3F). This light dose induced abundant filopodia formation within 30 minutes in 78% of cells expressing N-I-N-CAAX (FIG. 3C and FIG. 9D). This response was light-dependent, as only 10% of cells expressing N-I-N-CAAX formed filopodia in the same time interval without illumination ($P<0.0001$ by Pearson $x^2$ test) (FIGS. 9A and 9D). Cells continued to exhibit filopodial mobility throughout 1 hour of observation and did not show blebbing that might indicate phototoxicity. Similarly, 90% of cells expressing K-I-N-CAAX formed abundant filopodia within 30 minutes after illumination (FIG. 3G, FIG. 9D), compared with 25% not exposed to light ($P<0.0001$ by Pearson $x^2$ test) (FIGS. 9B and 9D). Illumination of K-CAAX-expressing cells did not induce filopodia (FIGS. 9C and 9D), confirming that the effect is not due to light alone. These results demonstrate that a protein caged by Dronpa fusion can be uncaged by light.

Figure 3H:
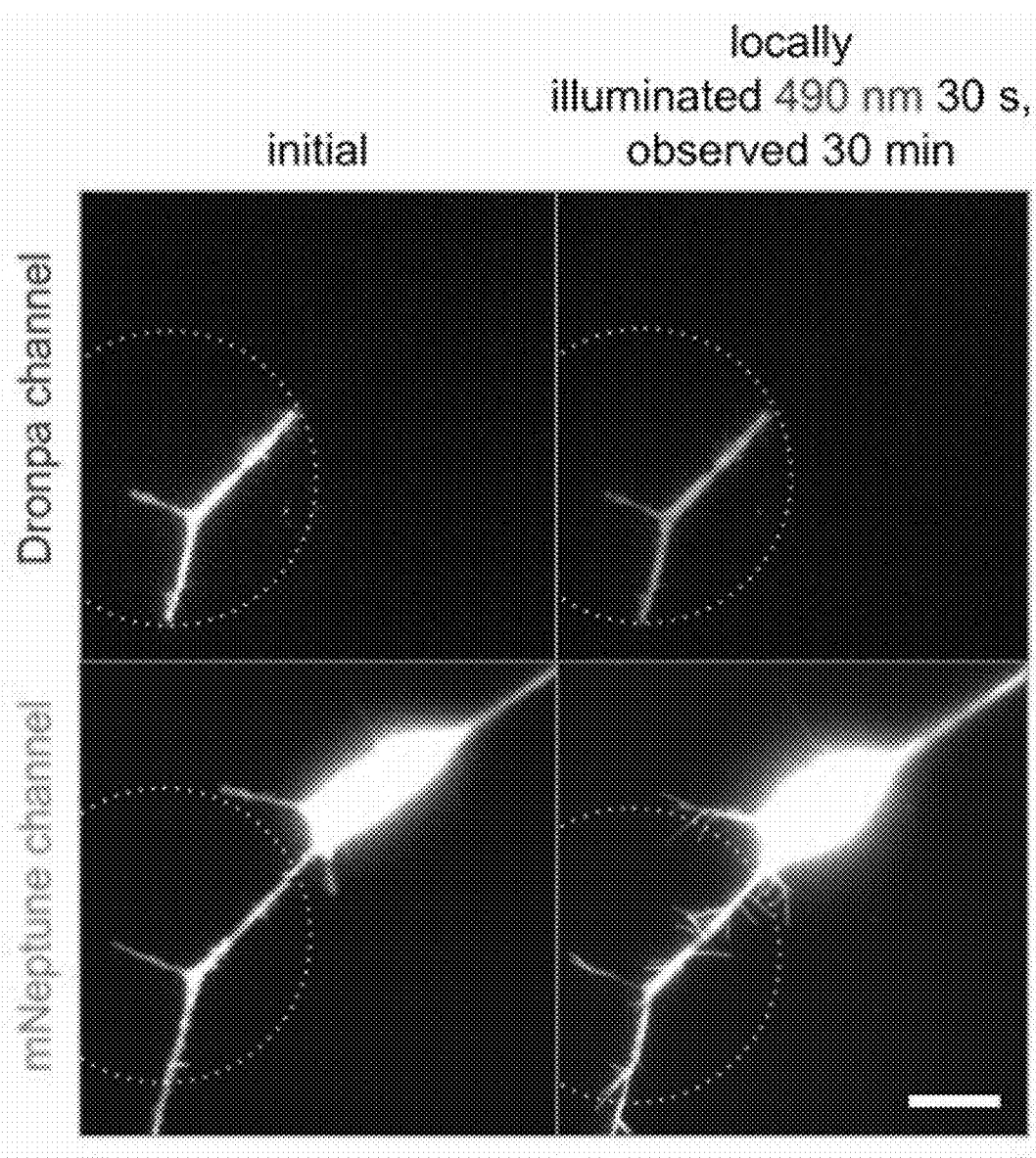
Figure 10:
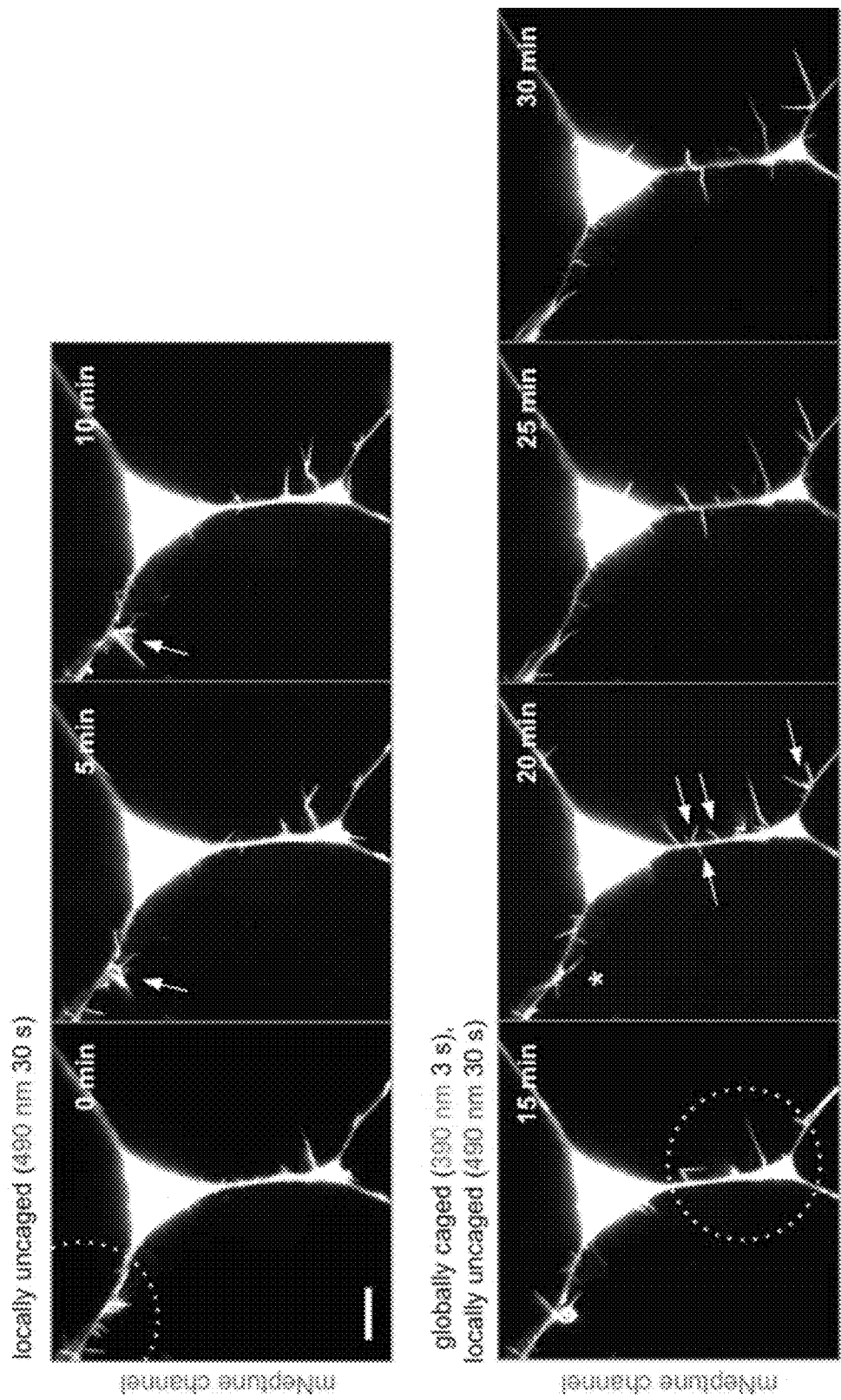
FIG. 10 shows temporal regulation of filopodia by light induction of intersectin activity. In a NIH3T3 cell expressing N-I-N-CAAX, local uncaging with 500 nm light (frame 1, dotted circle) induced local filopodia formation in 10 minutes (arrow, frames 2-3). The cell was then globally illuminated with 400 nm light to recage N-I-N-CAAX, then local uncaging was performed in a new location with 500 nm light (frame 4, dotted circle). Filopodia in the first uncaging location subsequently retracted (asterisk) while new filopodia formed in the second uncaging location (arrows, frames 5-7). The scale bar is 20 µm.

We investigated whether caged intersectin constructs could control filopodia formation with spatial or temporal specificity. First, we performed local illumination (490/20-nm light for 30 seconds) to portions of cells expressing N-I-N-CAAX or K-IN-CAAX and observed that filopodia appeared specifically in the illuminated regions (FIGS. 3D and 3H). We next tested whether light could induce filopodia in different locations at different times in one cell. We applied a 30-second uncaging pulse of cyan light at one subcellular region, a 3-second global recaging pulse of violet light, and finally another 30-second uncaging pulse at a different subcellular region. After the first uncaging pulse, filopodia appeared in the first region, whereas after the global recaging and second uncaging pulse, filopodia appeared in the second region simultaneous with retraction in the first region (FIG. 10).

Figure 11:
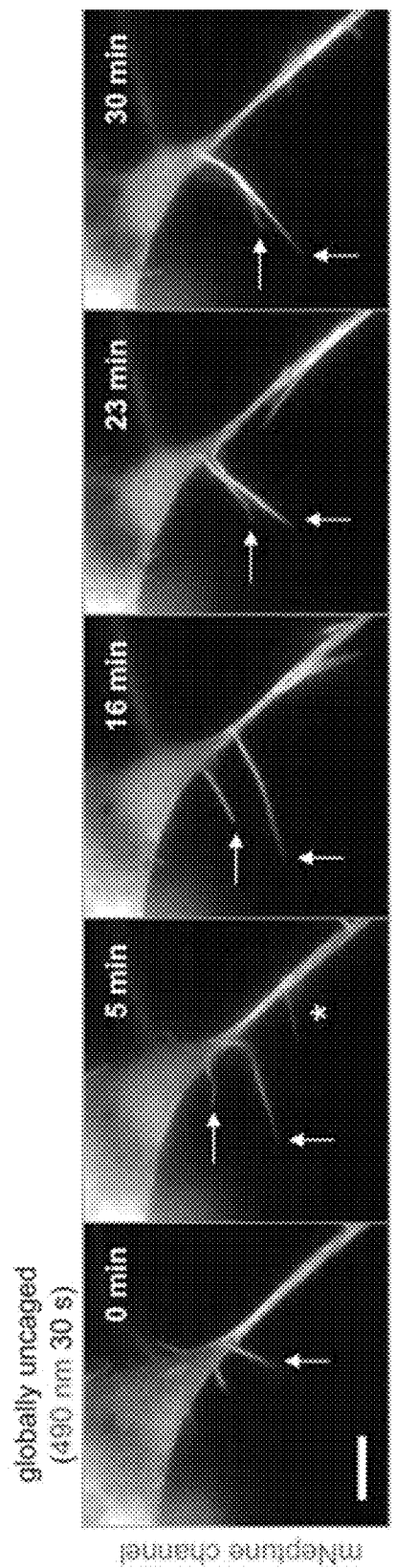
FIG. 11 shows that optical induction of intersectin reveals a role for Cdc42 in filopodia elongation. Uncaging of K-I-N-CAAX in a cell expressing preexisting filopodia (arrows) results in lengthening of the filopodia. New filopodia formation can also be observed (asterisk). The scale bar is 20 µm.

Whether Cdc42 activation can lengthen existing filopodia has been unclear, as Cdc42 effectors that promote filopodia extension rather than initiation have not been found. Rapid induction of intersectin activity by light allowed us to address this question. We observed that photouncaging of intersectin caused lengthening of many preexisting filopodia (FIG. 11). This suggests that models in which Cdc42 governs only filopodia initiation are incomplete (Faix et al. (2009) Int. J. Biochem. Cell Biol. 41:1656-1664) and that effectors may exist that promote filopodia extension analogous to how FMNL2 promotes lamellipodia extension downstream of Cdc42 (Block et al. (2012) Curr. Biol. 22:1005-1112).

An attractive feature of our design is potential generalizability. Other methods for optical control of single polypeptides, such as fusion to xanthopsin or phototropin, require extensive screening to achieve coupling of light-induced conformational changes to protein activation and, thus, have been applied to only a few targets (Fan et al. (2011) Biochemistry 50:1226-1237; Wu et al. (2009) Nature 461:104-108; Strickland et al. (2010) Nat. Methods 7:623-626). Our caged protein design does not require precise linkages; therefore, it should be more easily generalizable. Proteases are a class of enzymes for which light activation has not yet been achieved. Unlike GTPases or kinases, proteases are not naturally regulated by membrane recruitment, preventing the use of reversible membrane targeting methods to control them. Hence, we investigated whether we could create a light-inducible protease by fusion to Dronpa domains. We chose to regulate the hepatitis C virus (HCV) NS3-4A protease because its high sequence specificity and lack of overt toxicity allows assessment of function in mammalian cells (Lin et al. (2008) Proc. Natl. Acad. Sci. U.S.A. 105:7744-7749). Furthermore, it is composed predominantly of $\beta$ strands and loops (Romano et al. (2010) Proc. Natl. Acad. Sci. U.S.A. 107:20986-20991), providing a structural contrast to the completely $\alpha$-helical DH domain (Snyder et al. (2002) Nat. Struct. Biol. 9:468-475).

Figure 4A:
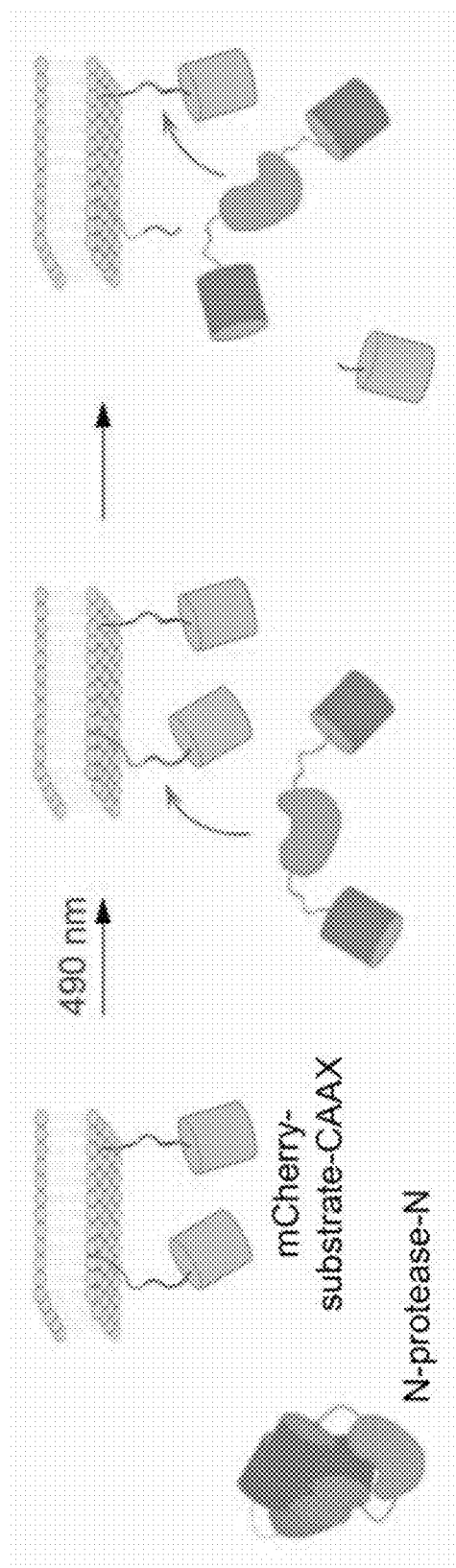
FIGS. 4A-4C show results with a light-inducible single-chain protease, N-protease-N (Dronpa145N-protease-Dronpa145N fusion).
Figure 4B:
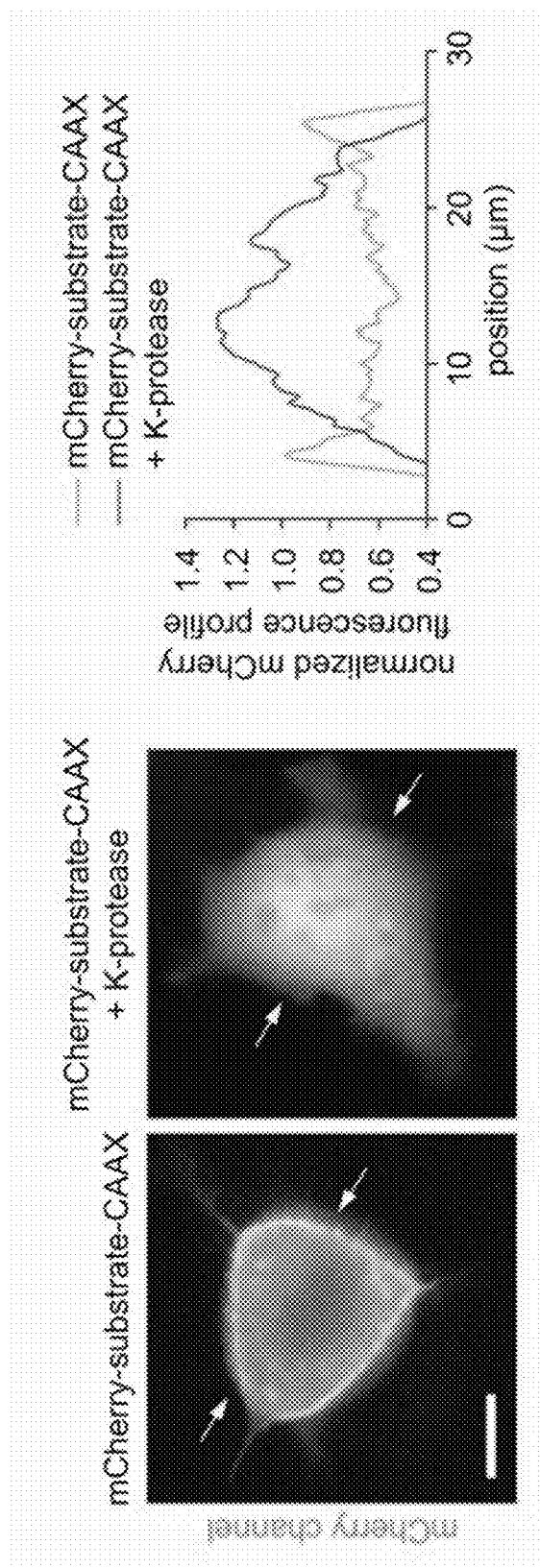
Figure 4C:
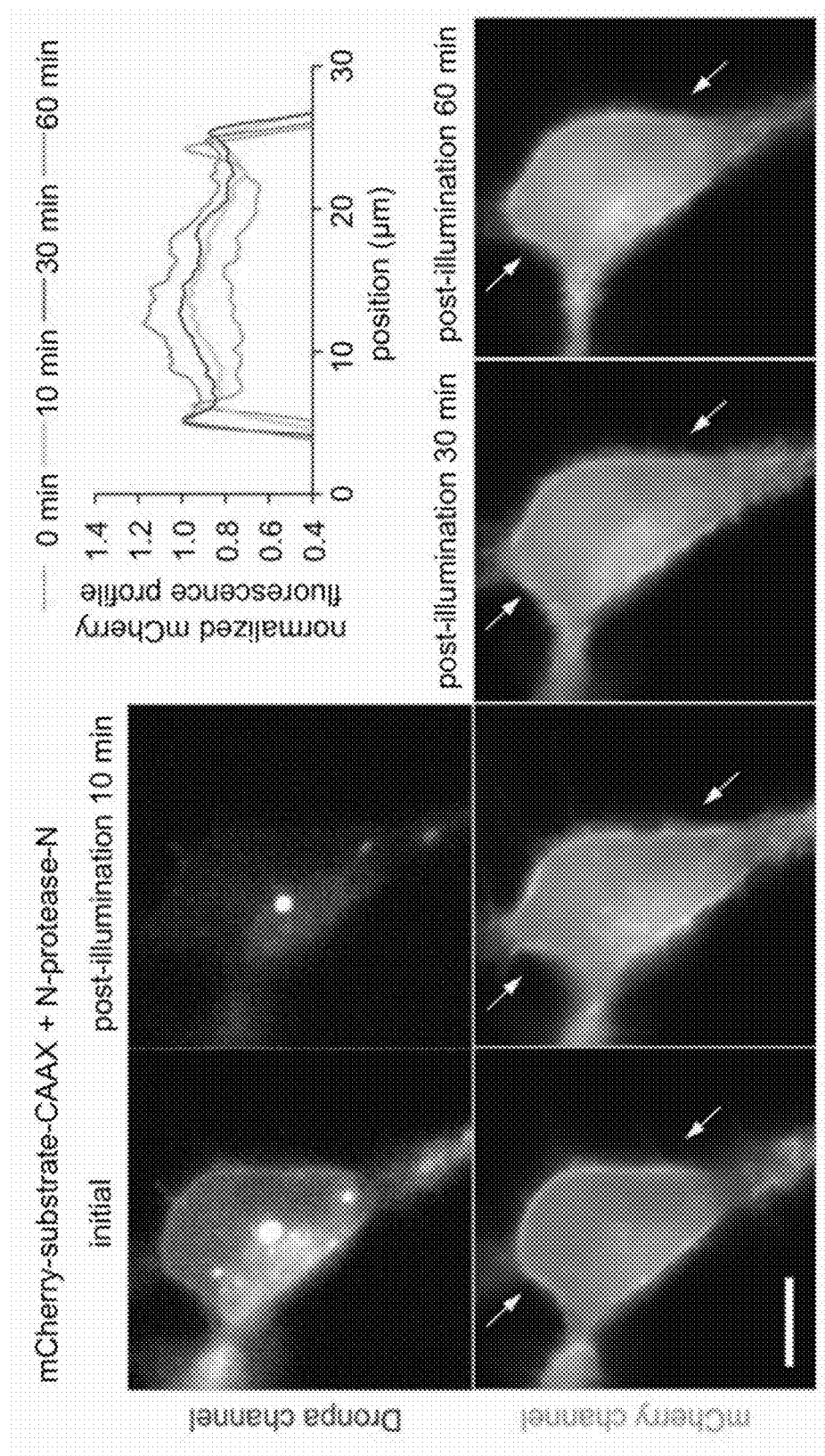
Figure 12A:
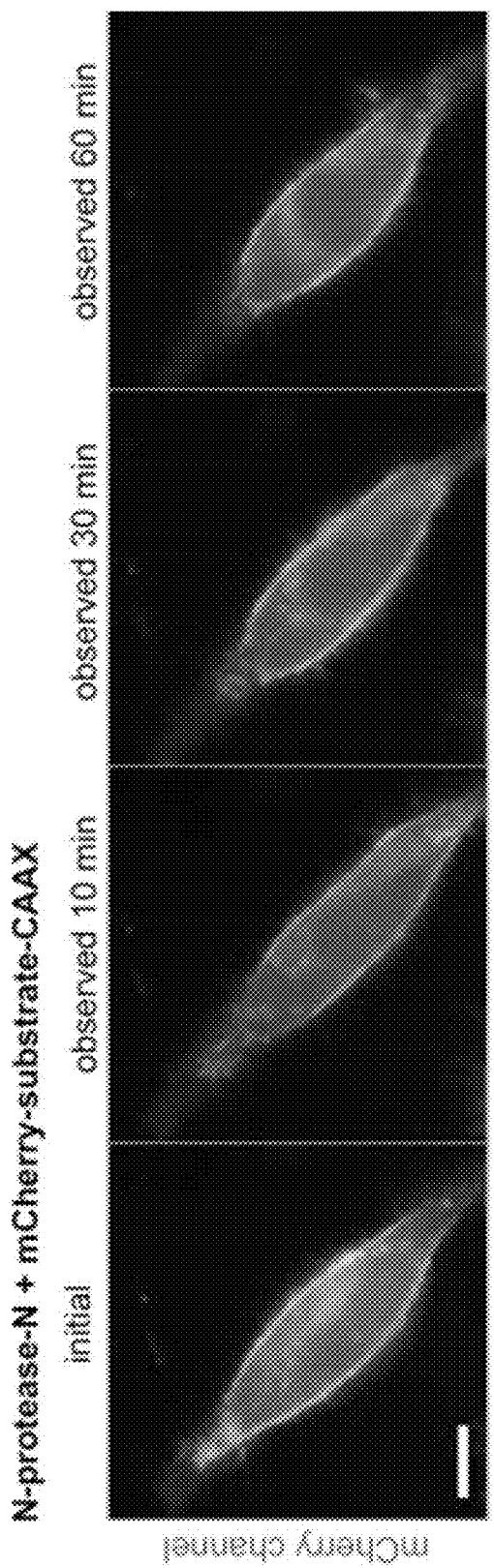
FIGS. 12A and 12B show that release of mCherry from the mCherry-substrate-CAAX fusion required both light and the caged protease.
Figure 12B:
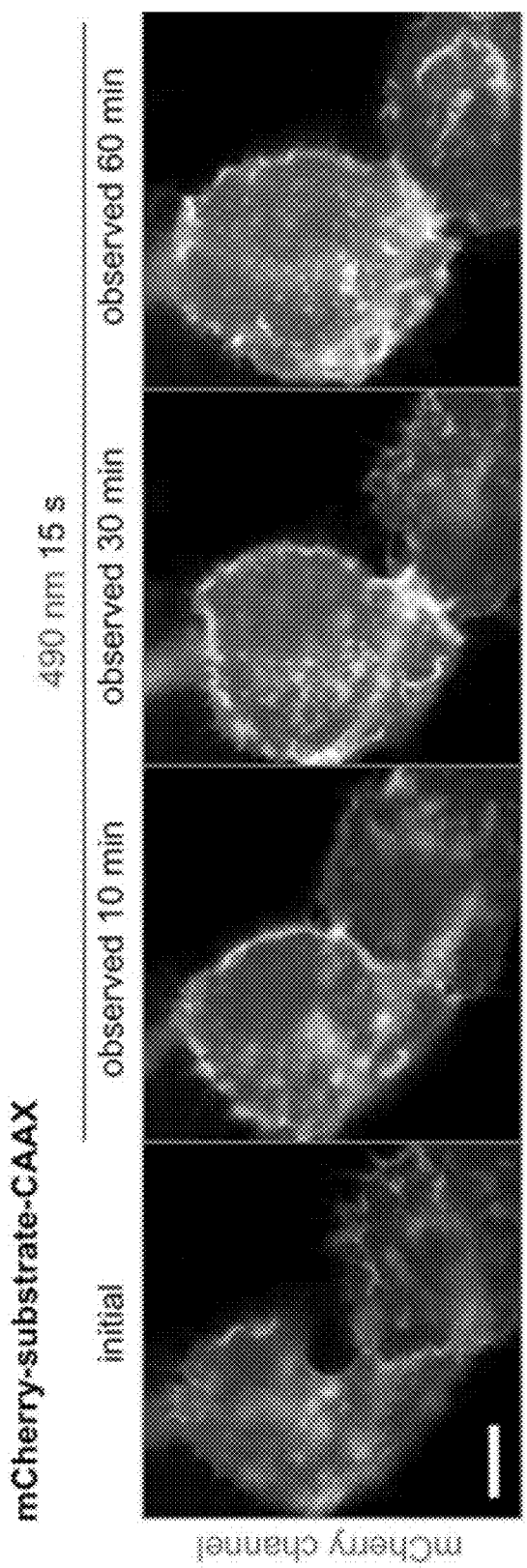

We constructed a Dronpa145N-protease-Dronpa145N fusion (N-protease-N) and, as a protease reporter, a fusion of mCherry, the NS4A/NS4B cleavage site of HCV polypeptide, and the CAAX-box farnesylation signal (mCherry-substrate-CAAX) (FIG. 4A). We expected that mCherry fluorescence would be released from the membrane into the cytosol by protease activity. Indeed, mCherry signal was membrane-bound in cells expressing mCherry-substrate-CAAX alone and cytoplasmic in cells coexpressing a positive control Dronpa145K-protease (FIG. 4B). We then used mCherry-substrate-CAAX to report light induction of N-protease-N. After off-switching of Dronpa fluorescence, cells showed an increase in cytosolic mCherry within 10 minutes, which continued to increase over 60 minutes (FIG. 4C). This response required illumination (FIG. 12A) and protease (FIG. 12B). Thus, the caged protein design can be used to control an enzyme domain that is not easily regulated by relocalization within the cell.

Since their discovery, FPs have seen widespread use exclusively as sensing tools. We discovered that photochromic FPs can have dual identities as optical sensors and light-controlled actuators. We have translated this discovery into a simple design for optically controllable proteins, which we propose to call FLIPs, for fluorescent light-inducible proteins. FLIPs also serve as their own reporters, as the photochromic FP domains report both protein localization and activity state. Thus, our results place photochromic FPs in a distinct central location in the optogenetic toolbox, integrating both sensing and controlling functions in a single protein class.

While the preferred embodiments of the invention have been illustrated and described, it will be appreciated that various changes can be made therein without departing from the spirit and scope of the invention.

What is claimed is:

1. A fusion protein comprising at least two photochromic polypeptides connected to a selected polypeptide of interest, wherein a first photochromic polypeptide is connected to the N-terminus of the selected polypeptide of interest and a second photochromic polypeptide is connected to the C-terminus of the selected polypeptide of interest, wherein the oligomerization state of the first photochromic polypeptide and the second photochromic polypeptide is controllable with light, wherein at least one photochromic polypeptide is a Dronpa polypeptide comprising an amino acid substitution at position 145 or a Padron polypeptide comprising an amino acid substitution at position 145, wherein the amino acid substitution at position 145 confers oligomerization characteristics, such that the first photochromic polypeptide and the second photochromic polypeptide are capable of associating with each other.

2. The fusion protein of claim 1, comprising two Dronpa-145N polypeptides or two Padron-145N polypeptides.

3. The fusion protein of claim 1, comprising a Dronpa-145K polypeptide and a Dronpa-145N polypeptide.

4. The fusion protein of claim 1, wherein at least one photochromic polypeptide comprises:
   a) an amino acid sequence selected from the group consisting of SEQ ID NOS:1, 3, and 5; or
   b) an amino acid sequence having at least 95% identity to an amino acid sequence selected from the group consisting of SEQ ID NOS:1, 3, and 5, wherein the photochromic polypeptide has fluorescence and oligomerization characteristics.

5. The fusion protein of claim 1, further comprising a targeting sequence.

6. The fusion protein of claim 1, further comprising a tag.

7. The fusion protein of claim 1, wherein the selected polypeptide of interest comprises a sequence from a protein selected from the group consisting of a membrane protein, a receptor, a hormone, a transport protein, a transcription factor, a cytoskeletal protein, an extracellular matrix protein, a signal-transduction protein, and an enzyme.

8. The fusion protein of claim 1, wherein the selected polypeptide of interest comprises a biologically active domain selected from the group consisting of a catalytic domain, a ligand binding domain, and a protein-protein interaction domain.

9. A method for controlling the activity of a selected polypeptide of interest with light, the method comprising:
   a) preparing a fusion protein according to claim 1; and
   b) illuminating the fusion protein with light at a wavelength that induces intramolecular dimerization of the first photochromic polypeptide and the second photochromic polypeptide, such that the activity of the selected polypeptide of interest is inactivated.

10. The method of claim 9, further comprising illuminating the fusion protein with light at a wavelength that induces dissociation of the first photochromic polypeptide from the second photochromic polypeptide, such that the activity of the selected polypeptide is restored.

11. The method of claim 9, further comprising visualizing the localization of the selected polypeptide by detecting fluorescence of the fusion protein resulting from the dimerization of the first photochromic polypeptide and the second photochromic polypeptide.

12. The method of claim 9, further comprising detecting inactivation of the selected polypeptide by measuring fluorescence from dimerization of the first photochromic polypeptide and the second photochromic polypeptide.

13. The method of claim 9, further comprising detecting inactivation of the selected polypeptide by measuring the activity of the selected polypeptide.

14. The method of claim 9, wherein fluorescence of the fusion protein is detected by a fluorometer, a fluorescence microscope, a fluorescence microplate reader, a fluorometric imaging plate reader, or fluorescence-activated cell sorting.

15. The method of claim 9, wherein the first photochromic polypeptide or the second photochromic polypeptide comprises:
   a) an amino acid sequence selected from the group consisting of SEQ ID NOS:1, 3, and 5; or
   b) an amino acid sequence having at least 95% identity to an amino acid sequence selected from the group consisting of SEQ ID NOS:1, 3, and 5, wherein the polypeptide has fluorescence and oligomerization characteristics.

16. A method for producing the fusion protein of claim 1, the method comprising:
   a) transforming a host cell with a recombinant polynucleotide comprising a polynucleotide encoding the fusion protein of claim 1 operably linked to a promoter;
   b) culturing the transformed host cell under conditions whereby the fusion protein is expressed; and
   c) isolating the fusion protein from the host cell.

17. A kit comprising the fusion protein of claim 1.

* * * * *